(12) United States Patent
Barrett et al.

(10) Patent No.: US 9,938,289 B2
(45) Date of Patent: Apr. 10, 2018

(54) THERAPEUTIC PYRAZOLYL THIENOPYRIDINES

(71) Applicant: THESAN PHARMACEUTICALS, INC., Carlsbad, CA (US)

(72) Inventors: Stephen D. Barrett, Hartland, MI (US); James B. Kramer, Sylvania, OH (US); Mark L. Boys, Lyons, CO (US); Huifen Chen, Burlingame, CA (US)

(73) Assignee: FBM THERAPEUTICS, LLC, Rancho Santa Fe, CA (US)

( * ) Notice: Subject to any disclaimer, the term of this patent is extended or adjusted under 35 U.S.C. 154(b) by 0 days.

(21) Appl. No.: 14/995,556

(22) Filed: Jan. 14, 2016

(65) Prior Publication Data

US 2016/0200735 A1   Jul. 14, 2016

Related U.S. Application Data

(60) Continuation of application No. 14/637,097, filed on Mar. 3, 2015, now Pat. No. 9,260,450, which is a continuation of application No. 13/864,457, filed on Apr. 17, 2013, now Pat. No. 9,090,625, which is a division of application No. 13/112,520, filed on May 20, 2011, now Pat. No. 8,455,512, which is a continuation of application No. 11/871,311, filed on Oct. 12, 2007, now Pat. No. 7,964,612.

(60) Provisional application No. 60/851,982, filed on Oct. 16, 2006.

(51) Int. Cl.
C07D 495/04     (2006.01)
A61K 9/14       (2006.01)
A61K 31/4365    (2006.01)
A61K 9/00       (2006.01)

(52) U.S. Cl.
CPC .......... *C07D 495/04* (2013.01); *A61K 9/0014* (2013.01); *A61K 31/4365* (2013.01)

(58) Field of Classification Search
CPC . C07D 495/04; A61K 9/0014; A61K 31/4365
See application file for complete search history.

(56) References Cited

U.S. PATENT DOCUMENTS 8,455,512 B2 *  6/2013  Barrett ................ C07D 495/04
                                                    514/301
9,260,450 B2 *  2/2016  Barrett ................ C07D 495/04

OTHER PUBLICATIONS

O'Kane, HV. et al. Transforming Growth Factor β's and Wound Healing. Pergamon, 1997, p. 63.*
Penn, JW. et al. The role of the TGF-β family in wound healing, burns, and scarring: a review. Int. J. Burn Trauma, 2012, 2(1), p. 18.*

* cited by examiner

*Primary Examiner* — Timothy R Rozof
(74) *Attorney, Agent, or Firm* — John P. White; Cooper & Dunham LLP

(57) ABSTRACT

The present invention provides for compounds of Formula I, and pharmaceutically acceptable salts thereof,

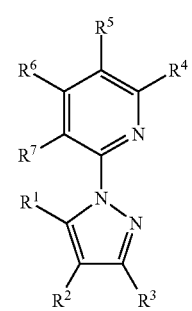

wherein $R^1$, $R^2$, $R^3$, $R^4$, $R^5$, $R^6$, and $R^7$ have any of the values defined therefor in the specification, and pharmaceutically acceptable salts thereof, that are useful as therapeutic agents in the treatment of TGFβ-mediated conditions, including cancer and fibrotic disorders. Also provided are pharmaceutical compositions comprising one or more compounds of Formula I.

17 Claims, No Drawings

THERAPEUTIC PYRAZOLYL THIENOPYRIDINES

CROSS-REFERENCE TO RELATED APPLICATIONS

This application is a continuation of U.S. Ser. No. 14/637,097, filed Mar. 3, 2015, now allowed, which is a continuation of U.S. Ser. No. 13/864,457, filed Apr. 17, 2013, now U.S. Pat. No. 9,090,625, issued Jul. 28, 2015, which is a divisional of U.S. Ser. No. 13/112,520, filed May 20, 2011, now U.S. Pat. No. 8,455,512, issued Jun. 4, 2013, which is a continuation of U.S. Ser. No, 11/871,311, filed Oct. 12, 2007, now U.S. Pat. No. 7,964,612, issued Jun. 21, 2011, which claims the benefit of U.S. Provisional Application No. 60/851,982, filed Oct. 16, 2006.

BACKGROUND OF THE INVENTION

TGF-β's (transforming growth factor-β's) activate fibrotic and tumor-promoting signaling cascades. Three mammalian TGFβ's, TGFβ$_1$, TGFβ$_2$, and TGFβ$_3$, can activate the TGFβ pathway. The TGFβ's bind to and signal through cell surface receptors (see Singh et al. (2004) Curr. Opin. Drug Disc. and Dev., 7: 437-445). A TGFβ first binds to a type II receptor (TβRII), which then binds to and phosphorylates a type I receptor (TβRI) (i.e., an activin receptor-like kinase (ALK)). There is a family of ALK proteins including ALK-5, which is the most specific ALK for TGFβ. Activation of ALK-5 leads to phosporylation of intracellular proteins, which results in the regulation of fibrosis and tumorigenesis. Therefore, the discovery of ALK-5 inhibitors is an active area of investigation to discover inhibitors to treat cancer, and conditions involving fibrosis (see Singh et al. (2004)).

One example of a condition that involves fibrosis is the formation of scars during wound repair. Scars, including hypertrophic and keloid scars, typically result from the deposition of collagen at wound sites. Wounds may be produced through many different kinds of mechanisms including surgery, accidental injuries, burns, trauma, etc. It has been reported that the application of TGFβ$_3$, antibodies to TGFβ$_1$ and TGFβ$_2$ which inhibit the TGFβ pathway can assist in reducing scarring (O'Kane and Ferguson, (1997) Int. J. Biochem. Cell Biol., 29: 63-78). Accordingly, there is an ongoing need in the art for small molecule ALK-5 inhibitors that can be used to reduce scar formation, and for the treatment of other fibrotic conditions, as well as cancer.

SUMMARY OF THE INVENTION

In one aspect, the present invention provides for compounds of formula I:

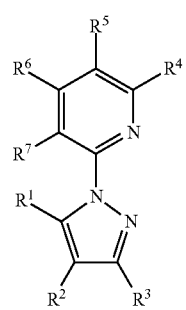

I or a pharmaceutically acceptable salt thereof, wherein: $R^1$ is a thieno[3,2-c]pyridinyl, a thieno[3,2-b]pyridinyl, a thieno [2,3-c]pyridinyl, or a thieno[2,3-b]pyridinyl, each of which may be optionally substituted with one to three substituents each independently selected from the group consisting of: —$C_1$-$C_3$-alkyl, —($C_1$-$C_3$-alkyl)-S—($C_1$-$C_3$-alkyl), —S—$C_1$-$C_3$-alkyl, —($C_1$-$C_3$-alkyl)-O—($C_1$-$C_3$-alkyl), —O—$C_1$-$C_3$-alkyl, —C(O)O—$C_1$-$C_3$-alkyl, —C(O)O—H, —C(O)NR$^{30}$R$^{31}$, halo, —CN, —OH, wherein R$^{30}$ and R$^{31}$ are each independently selected from the group consisting of: H, and —$C_1$-$C_3$ alkyl-OH, —$C_1$-$C_3$-alkyl, halo, and —O—$C_1$-$C_3$-alkyl; R$^2$ and R$^3$ are independently selected from the group consisting of: hydrogen, —$C_1$-$C_3$-alkyl, —($C_1$-$C_3$-alkyl)-S—($C_1$-$C_3$-alkyl), —S—$C_1$-$C_3$-alkyl, —($C_1$-$C_3$-alkyl)-O—($C_1$-$C_3$-alkyl), —O—$C_1$-$C_3$-alkyl, —C(O)O—$C_1$-$C_3$-alkyl, —C(O)O—H, —C(O)NR$^{30}$R$^{31}$, halo, —CN, —OH, and a $C_3$-$C_6$-cycloalkyl, wherein R$^{30}$ and R$^{31}$ are each independently selected from the group consisting of: H, and —$C_1$-$C_3$ alkyl; or R$^2$ and R$^3$ may be taken together to form a 5 or 6-membered heteroaryl, a phenyl, a $C_4$-$C_6$-cycloalkyl, or a 4-6-membered heterocycloalkyl, wherein said $C_4$-$C_6$-cycloalkyl or 4-6-membered heterocycloalkyl may be optionally substituted with one to three substituents independently selected from halo, —OH, oxo, and —$C_1$-$C_3$ alkyl, wherein said 5 or 6-membered heteroaryl, or phenyl may be optionally substituted with one to three substituents independently selected from halo, —CN, —OH, —O—$C_1$-$C_3$ alkyl and —$C_1$-$C_3$ alkyl; and R$^4$, R$^5$, R$^6$, and R$^7$ are selected from the group consisting of: H, —OH, $C_3$-cycloalkyl, —$C_1$-$C_3$-alkyl, —($C_1$-$C_3$-alkyl)-S—($C_1$-$C_3$-alkyl), —S—$C_1$-$C_3$-alkyl, —($C_1$-$C_3$-alkyl)-O—($C_1$-$C_3$-alkyl), —O—$C_1$-$C_3$-alkyl, —C(O)O—$C_1$-$C_3$-alkyl, —C(O)O—H, —C(O)NR$^{30}$R$^{31}$, halo, —CN, —OH, wherein R$^{30}$ and R$^{31}$ are each independently selected from the group consisting of: H, and —$C_1$-$C_3$ alkyl, —O—$C_1$-$C_3$-alkyl, and halo.

In certain embodiments, $R^1$ is a thieno[3,2-c]pyridinyl, which may be optionally substituted as specified herein. The positions of a thieno[3,2-c]pyridine are numbered as follows:

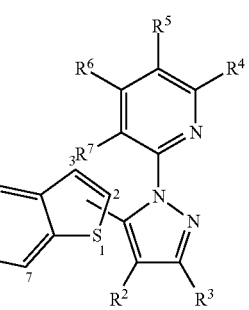

A thieno[3,2-c]pyridinyl is a monovalent radical of thieno [3,2-c]pyridine. Thus, in certain embodiments of the present invention, are compounds of formula II:

II wherein $R^1$, $R^2$, $R^3$, $R^4$, $R^5$, $R^6$, and $R^7$ have any of the values specified herein, and wherein the thieno[3,2-c] radical is attached at any of positions 2, 3, 4, 6, or 7.

In certain embodiments, $R^1$ is a thieno[2,3-c]pyridinyl, which may be optionally substituted as specified. The positions of a thieno[2,3-c]pyridine are numbered as follows:

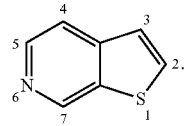

A thieno[2,3-c]pyridinyl is a monovalent radical of thieno[2,3-c]pyridine. Thus, in certain embodiments of the present invention, are compounds of formula III:

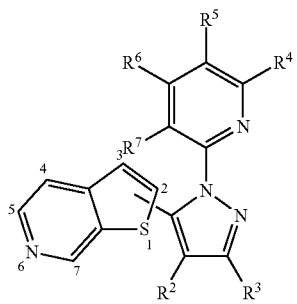

wherein $R^1$, $R^2$, $R^3$, $R^4$, $R^5$, $R^6$, and $R^7$ have any of the values specified herein, and wherein the thieno[2,3-c] radical is attached at any of positions 2, 3, 4, 5, or 7.

In certain embodiments, $R^1$ is a thieno[2,3-b]pyridinyl, which may be optionally substituted as specified herein. The positions of a thieno[2,3-b]pyridine are numbered as follows:

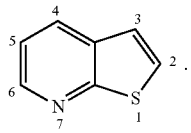

A thieno[2,3-b]pyridinyl is a monovalent radical of thieno[2,3-c]pyridine. Thus, in certain embodiments of the present invention, are compounds of formula IV:

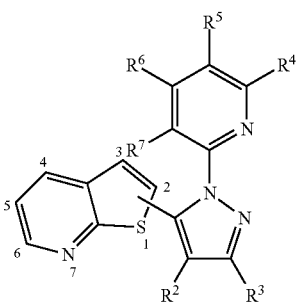

wherein $R^1$, $R^2$, $R^3$, $R^4$, $R^5$, $R^6$, and $R^7$ have any of the values specified herein, and wherein the thieno[2,3-b] radical is attached at any of positions 2, 3, 4, 5, or 6.

In certain embodiments, $R^1$ is a thieno[3,2-b]pyridinyl, which may be optionally substituted as specified herein. The positions of a thieno[3,2-b]pyridine are numbered as follows:

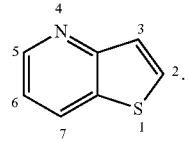

A thieno[3,2-b]pyridinyl is a monovalent radical of thieno[3,2-c]pyridine. Thus, in certain embodiments of the present invention, are compounds of formula V:

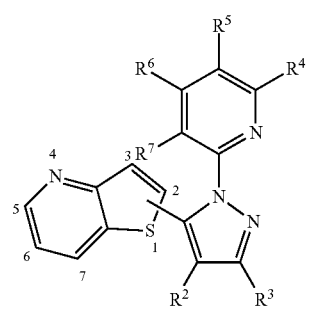

wherein $R^1$, $R^2$, $R^3$, $R^4$, $R^5$, $R^6$, and $R^7$ have any of the values specified herein, and wherein the thieno[3,2-b] radical is attached at any of positions 2, 3, 5, 6, or 7.

In certain embodiments, $R^1$ is a thieno[3,2-c]pyridinyl or a thieno[2,3-c]pyridinyl.

In certain embodiments, $R^1$ is a thieno[3,2-c]pyridinyl or a thieno[2,3-c]pyridinyl, which may be optionally substituted with one to three substituents each independently selected from the group consisting of: $C_1$-$C_3$-alkyl, —($C_1$-$C_3$-alkyl)-S—($C_1$-$C_3$-alkyl), —S—$C_1$-$C_3$-alkyl, —($C_1$-$C_3$-alkyl)-O—($C_1$-$C_3$-alkyl), —O—$C_1$-$C_3$-alkyl, —C(O)O—$C_1$-$C_3$-alkyl, —C(O)O—H, —C(O)NR$^{30}$R$^{31}$, halo, —CN, —OH, wherein $R^{30}$ and $R^{31}$ are each independently selected from the group consisting of: H, and $C_1$-$C_3$ alkyl-OH, $C_1$-$C_3$-alkyl, halo, and —O—$C_1$-$C_3$-alkyl;

In certain embodiments, $R^1$ is a thieno[3,2-c]pyridinyl or a thieno[2,3-c]pyridinyl, which may be optionally substituted with one to three substituents each independently selected from the group consisting of: —OH, $C_1$-$C_3$ alkyl, halo, and —O—$C_1$-$C_3$ alkyl.

In certain embodiments, $R^2$ and $R^3$ are taken together to form a $C_4$-$C_8$-cycloalkyl, or a 4-6-membered heterocycloalkyl, wherein said $C_4$-$C_6$-cycloalkyl or 4-6-membered heterocycloalkyl may be optionally substituted with one to three substituents independently selected from oxo and $C_1$-$C_3$ alkyl. In other embodiments, $R^2$ and $R^3$ are taken together to form a $C_5$-cycloalkyl, or a 4-6-membered heterocycloalkyl, wherein said 4-6-membered heterocycloalkyl is selected from the group consisting of: a tetrahydrofuranyl, a tetrahydrothienyl, a imidazolidinyl, an oxazolidinyl, an imidazolinyl, an isoxazolidinyl, and a pyrrolidinyl. In other embodiments, $R^2$ and $R^3$ are taken together to form a $C_5$-cycloalkyl and $R^1$ is a thieno[3,2-c]pyridinyl or a thieno[2,3-c]pyridinyl.

In certain embodiments, a compound of the present invention is (2-(6-methylpyridin-2-yl)-2,4,5,6-tetrahydrocyclopenta[c]pyrazol-3-yl)thieno[3,2-c]pyridine, or a pharmaceutically acceptable salt thereof.

In certain embodiments, a compound of the present invention is 2-(2-(6-methylpyridin-2-yl)-2,4,5,6-tetrahydrocyclopenta[c]pyrazol-3-yl)thieno[2,3-c]pyridine, or a pharmaceutically acceptable salt thereof.

In other embodiments, $R^2$ and $R^3$ are independently selected from the group consisting of: hydrogen, $C_1$-$C_3$-alkyl, —($C_1$-$C_3$-alkyl)-O—($C_1$-$C_3$-alkyl), —O—$C_1$-$C_3$-alkyl, —C(O)O—$C_1$-$C_3$-alkyl, —C(O)O—H, —C(O)NR$^{30}$R$^{31}$, halo, —CN, —OH, and a $C_3$-$C_6$-cycloalkyl, wherein $R^{30}$ and $R^{31}$ are each independently selected from the group consisting of: H, and $C_1$-$C_3$ alkyl. In particular embodiments, $R^2$ and $R^3$ are independently selected from the group consisting of: hydrogen, and $C_1$-$C_3$ alkyl. In more particular embodiments, $R^2$ is $C_1$-$C_2$ alkyl and $R^3$ is hydrogen.

In certain embodiments, $R^5$, $R^6$, and $R^7$ are H, and $R^4$ is $C_1$-$C_3$-alkyl. In yet other embodiments, $R^4$ is methyl. In certain embodiments, $R^5$, $R^6$, and $R^7$ are H, and $R^4$ is methyl.

In certain embodiments, $R^1$ is a thieno[3,2-c]pyridinyl or a thieno[2,3-c]pyridinyl, which may be optionally substituted with one to three substituents each independently selected from the group consisting of: —OH, $C_1$-$C_3$ alkyl, halo, and —O—$C_1$-$C_3$ alkyl. In certain embodiments, $R^1$ is a thieno[3,2-c]pyridin-2-yl or a thieno[2,3-c]pyridin-2-yl, which may be optionally substituted with one to three substituents each independently selected from the group consisting of: —OH, $C_1$-$C_3$ alkyl, halo, and —O—$C_1$-$C_3$ alkyl. In certain embodiments, $R^1$ is a thieno[3,2-c]pyridine-2-yl, which may be optionally substituted with one to three substituents each independently selected from the group consisting of: —OH, $C_1$-$C_3$ alkyl, halo, and —O—$C_1$-$C_3$ alkyl. In particular embodiments, $R^1$ is thieno[3,2-c]pyridinyl-2yl.

In certain embodiments,

In certain embodiments, $R^5$, $R^6$, and $R^7$ are H; $R^4$ is a $C_1$-$C_3$-alkyl; and $R^1$ is a thieno[3,2-c]pyridinyl or a thieno[2,3-c]pyridinyl, which may be optionally substituted with one to three substituents each independently selected from the group consisting of: —OH, $C_1$-$C_3$ alkyl, halo, and —O—$C_1$-$C_3$ alkyl. In certain embodiments, $R^5$, $R^6$, and $R^7$ are H; $R^4$ is methyl; and $R^1$ is a thieno[3,2-c]pyridinyl or a thieno[2,3-c]pyridinyl, which may be optionally substituted with one to three substituents each independently selected from the group consisting of: —OH, $C_1$-$C_3$ alkyl, halo, and —O—$C_1$-$C_3$ alkyl. In certain embodiments, $R^5$, $R^6$, and $R^7$ are H; $R^4$ is methyl; and $R^1$ is a thieno[3,2-c]pyridinyl or a thieno[2,3-c]pyridinyl. In certain embodiments, $R^5$, $R^6$, and $R^7$ are H; $R^4$ is methyl; and R' is a thieno[2,3-c]pyridinyl. In certain embodiments, $R^5$, $R^8$, and $R^7$ are H; $R^4$ is methyl; and is a thieno[3,2-c]pyridinyl.

In certain embodiments, $R^5$, $R^6$, and $R^7$ are H; $R^4$ is methyl; $R^1$ is a thieno[2,3-c]pyridinyl; and $R^2$ and $R^3$ are independently selected from the group consisting of: hydrogen, and $C_1$-$C_3$ alkyl.

In certain embodiments, $R^5$, $R^6$, and $R^7$ are H; $R^4$ is methyl; $R^1$ is a thieno[3,2-c]pyridinyl; and $R^2$ and $R^3$ are independently selected from the group consisting of: hydrogen, and $C_1$-$C_3$ alkyl.

In certain embodiments, $R^5$, $R^6$, and $R^7$ are H; $R^4$ is methyl; R' is a thieno[2,3-c]pyridin-2-yl; and $R^2$ and $R^3$ are independently selected from the group consisting of: hydrogen, and $C_1$-$C_3$ alkyl.

In certain embodiments, $R^5$, $R^6$, and $R^7$ are H; $R^4$ is methyl; $R^1$ is a thieno[3,2-c]pyridin-2-yl; and $R^2$ and $R^3$ are independently selected from the group consisting of: hydrogen, and $C_1$-$C_3$ alkyl.

Examples of compounds of formula I include:
2-[1-(6-methylpyridin-2-yl)-1H-pyrazol-5-yl]thieno[3,2-c]pyridine;
2-[3,4-dimethyl-1-(6-methylpyridin-2-yl)-1H-pyrazol-5-yl]thieno[3,2-c]pyridine;
2-[3-methyl-1-(6-methylpyridin-2-yl)-1H-pyrazol-5-yl]thieno[3,2-c]pyridine;
2-[3-ethyl-1-(6-methylpyridin-2-yl)-1H-pyrazol-5-yl]thieno[3,2-c]pyridine;
2-[4-ethyl-1-(6-methylpyridin-2-yl)-1H-pyrazol-5-yl]thieno[3,2-c]pyridine; and pharmaceutically acceptable salts thereof.

Another example of a compound of formula I is 2-[4-methyl-1-(6-methylpyridin-2-yl)-1H-pyrazol-5-yl]thieno[3,2-c]pyridine; and pharmaceutically acceptable salts thereof. In one particular embodiment, the compound is 2-[4-methyl-1-(6-methylpyridin-2-yl)-1H-pyrazol-5-yl]thieno[3,2-c]pyridine.

Another example of a compound of formula I is 2-(4-methyl-1-(6-methylpyridin-2-yl)-1H-pyrazol-5-yl)thieno[2,3-c]pyridine, or a pharmaceutically acceptable salt thereof.

In another aspect, the present invention provides for methods of reducing scar formation, comprising administering to a mammal in need of such treatment a therapeutically effective amount of a compound of formula I, or a pharmaceutically acceptable salt thereof. In certain embodiments, the compound of formula I is administered topically. In certain embodiments, the compound of formula I is 2-[4-methyl-1-(6-methylpyridin-2-yl)-1H-pyrazol-5-yl]thieno[3,2-c]pyridine; or a pharmaceutically acceptable salt thereof.

In certain embodiments, the present invention provides for methods of reducing existing scars, comprising administering to a mammal in need of such treatment a therapeutically effective amount of a compound of formula I, or a pharmaceutically acceptable salt thereof.

In certain embodiments, 2-[4-methyl-1-(6-methylpyridin-2-yl)-1H-pyrazol-5-yl]thieno[3,2-c]pyridine; or a pharmaceutically acceptable salt thereof, may be used in the in the manufacture of a medicament for the inhibition of scar formation.

In another aspect, the present invention provides for methods of treating a TGFβ-mediated conditions, comprising administering to a mammal in need of such treatment a therapeutically effective amount of a compound of formula I, or a pharmaceutically acceptable salt thereof. In certain embodiments, the TGFβ-mediated condition is selected from the group comprising: cancer, breast cancer, lung cancer, colon cancer, prostate cancer, ovarian cancer, pancreatic cancer, melanoma, fibrotic diseases, glomerulonephritis, diabetic nephropathy, hepatic fibrosis, pulmonary fibrosis, arterial hyperplasia, restenosis, scleroderma, and dermal scarring. In certain embodiments, the TGFβ-mediated condition is dermal scarring. In certain embodiments, the compound of formula I is 2-[4-methyl-1-(6-methylpyridin-2-yl)-1H-pyrazol-5-yl]thieno[3,2-c]pyridine; or a pharmaceutically acceptable salt thereof. In certain embodiments, the TGFβ-mediated condition is dermal scarring and the compound of formula I is 2-[4-methyl-1-(6-methylpyridin-2-yl)-1H-pyrazol-5-yl]thieno[3,2-c]pyridine; or a pharmaceutically acceptable salt thereof.

In another aspect, the present invention provides for pharmaceutical compositions comprising: a therapeutically effective amount of a compound of formula I and a pharmaceutically acceptable excipient. In certain embodiments, the compound of formula I is 2-[4-methyl-1-(6-methylpyridin-2-yl)-1H-pyrazol-5-yl]thieno[3,2-c]pyridine; or a pharmaceutically acceptable salt thereof.

In another aspect, the present invention provides for topical pharmaceutical compositions comprising: a therapeutically effective amount of a compound of formula I, or pharmaceutically acceptable salt thereof, and a pharmaceutically acceptable excipient suitable for topical application. In certain embodiments, the compound of formula I is 2-[4-methyl-1-(6-methylpyridin-2-yl)-1H-pyrazol-5-yl]thieno[3,2-c]pyridine; or a pharmaceutically acceptable salt thereof.

In a further embodiment, the invention is directed to a kit containing at least one of the compounds of the present invention packaged for retail distribution, in association with instructions advising the consumer on how to use the compound to alleviate a TGFβ-mediated condition. An additional embodiment is directed to the use of a compound as a diagnostic agent to detect inappropriate activation of a TGFβ activated pathway.

DEFINITIONS

As used throughout this application, including the claims, the following terms have the meanings defined below, unless specifically indicated otherwise.

The plural and singular should be treated as interchangeable, other than the indication of number.

A "scar" is a mark that is present after wound repair at the site of a wound. The term "scar" includes keloid scars, hypertrophic scars, and scars that are predominantly not elevated and predominantly do not grow beyond the boundaries of the original wound.

A "keloid scar" is an overgrowth of scar tissue at a wound site, that typically grows beyond the boundaries of the original wound.

A "hypertrophic scar" is an elevated scar that predominantly does not grow beyond the boundaries of the original wound.

The term "wound" refers to an injury that disrupts the normal integrity of a tissue, such as skin. A "wound" may intentionally or accidentally occur. Examples of wounds include lacerations, contused wounds, closed wounds, open wounds, perforated wounds, incised wounds, puncture wounds, burns, etc.

The terms "compound of Formula I", "compounds of the invention", and "compounds" are used interchangeably throughout the application and should be treated as synonyms.

The term "patient" refers to warm blooded animals such as, for example, guinea pigs, mice, rats, gerbils, cats, rabbits, dogs, monkeys, chimpanzees, stump tail macaques, and humans.

The term "treat" refers to the ability of the compounds to relieve, alleviate, or slow the progression of the patient's disease (or condition) or any tissue damage associated with the disease.

The term "mammal" refers to a member of the class Mammalia. Examples of mammals include, without limitation, humans, primates, chimpanzees, rodents, mice, rats, rabbits, horses, livestock, dogs, cats, sheep and cows. In one particular embodiment, a mammal is a human.

The term "isomer" means "stereoisomer" and "geometric isomer" as defined below.

The term "stereoisomer" means compounds that possess one or more chiral centers and each center may exist in the R or S configuration. Stereoisomers include all diastereomeric, enantiomeric and epimeric forms as well as racemates and mixtures thereof.

The term "geometric isomer" means compounds that may exist in cis, trans, anti, entgegen (E), and zusammen (Z) forms as well as mixtures thereof.

Certain of the compounds of the formula (I) may exist as geometric isomers. The compounds of the formula (I) may possess one or more asymmetric centers, thus existing as two, or more, stereoisomeric forms. The present invention includes all the individual stereoisomers and geometric isomers of the compounds of formula (I) and mixtures thereof. Individual enantiomers can be obtained by chiral separation, by using available synthetic building blocks incorporating the relevant asymmetric center with the appropriate stereochemistry in the synthesis, or by asymmetric synthesis starting with achiral synthetic building blocks.

Certain compounds of the present invention may exist as tautomeric forms. All such tautomeric forms are included within the scope of the present invention.

In addition, the compounds of the present invention can exist in unsolvated as well as solvated forms, including hydrated forms, with pharmaceutically acceptable solvents such as water, ethanol, and the like. The compounds may also exist in one or more crystalline states, i.e. polymorphs, or they may exist as amorphous solids. All such forms are intended to be encompassed within the scope of the present invention.

The term "alkyl group" or "alkyl" means a monovalent radical of a straight or branched chain alkane. For example, a "$C_{1-3}$ alkyl" is an alkyl group having from 1 to 3 carbon atoms. Examples of $C_1$-$C_3$ straight-chain alkyl groups include methyl, ethyl, and n-propyl. Examples of branched-chain $C_1$-$C_3$ alkyl groups include isopropyl. The term alkyl includes both "unsubstituted alkyls" and "substituted alkyls," the latter of which refers to alkyl groups having substituents replacing a hydrogen on one or more carbons (e.g., one to six substituents) of the hydrocarbon backbone. Such substituents may be independently selected from the group consisting of: halo, I, Br, $Cl_2$, F, —OH, —COOH, and —$NH_2$.

Typical substituted $C_1$-$C_3$ straight-chain alkyl groups include 2-chloropropyl, 2-hydroxy-ethyl, 2-aminopropyl, and trifluoromethyl.

The term "$C_3$-$C_6$cycloalkyl" refers to a monovalent radical of a monocyclic alkane containing from 3 to 6 carbons. Examples of "$C_3$-$C_6$cycloalkyls" include cyclopropyl, cyclobutyl, cyclopentyl, and cyclohexyl.

The term "$C_4$-$C_6$cycloalkyl" refers to a monovalent radical of a monocyclic alkane containing from 4 to 6 carbons. Examples of "$C_4$-$C_6$cycloalkyls" include cyclobutyl, cyclopentyl, and cyclohexyl.

A "4-6-membered heterocycloalkyl" refers to a monovalent radical of a 4-6 membered monocyclic heterocycloalkane.

A 4-membered heterocycloalkyl is a 4-membered ring containing 3 carbons and a heteroatom selected from oxygen, nitrogen, sulfur. The sulfur may also be present as $S(O)$ or $S(O)_2$. Examples of 4-membered heterocycloalkyl groups include oxetanyl, thietanyl, and azetidinyl.

A 5-membered, heterocycloalkyl contains from 2 to 4 carbon atoms and from 1 to 3 heteroatoms selected from the group consisting of: 1 O; 1 S; 1 N; 2 N; 1 S and 1 N; 1 S and 2 N; 1 O and 1 N; and 1 O and 2 N, wherein when two O atoms or one O atom and one S atom are present in a ring, the two O atoms or one O atom and one S atom are not bonded directly to each other. A sulfur may also be present as S(O) or S(O)$_2$. Examples of 5-membered heterocycloalkyls include tetrahydrofuranyl, tetrahydrothienyl, imidazolidinyl, oxazolidinyl, imidazolinyl, isoxazolidinyl, and pyrrolidinyl.

A "6-membered heterocycloalkyl" contains from 3 to 5 carbon atoms and from 1 to 3 heteroatoms selected from the group consisting of: 1 O; 2 O; 1 S; 2 S; 1 N; 2 N; 3 N; 1 S, 1 O and 1 N; 1 S and 1 N; 1 S and 2 N; 1 S and 1 O; 1 S and 2 O; 1 O and 1 N; and 1 O and 2 N, wherein when two O atoms or one O atom and one S atom are present, the two O atoms or one O atom and one S atom are not bonded directly to each other. A sulfur may also be present as S(O) or S(O)$_2$. Examples of 6-membered heterocycloalkyls include tetrahydropyranyl, dioxanyl, 1,3-dioxolanyl, 1,4-dithianyl, hexahydropyrimidine, morpholinyl, piperazinyl, piperidinyl, pyrazolidinyl, pyrazolinyl, 1,2,3,6-tetrahydropyridinyl, tetrahydrothiopyranyl, 1,1-dioxo-hexahydro-1λ$^6$-thiopyranyl, 1,1-dioxo-1λ$^6$-thiomorpholinyl, thiomorpholinyl, thioxanyl, and 1,3,5-trithianyl.

A "5-membered heteroaryl" is a 5-membered, monocyclic, aromatic ring radial having from 2 to 4 carbon atoms and from 1 to 3 heteroatoms selected from the group consisting of: 1 O; 1 S; 1 N; 2 N; 3 N; 1 S and 1 N; 1 S and 2 N; 1 O and 1 N; and 1 O and 2 N. In certain embodiments, a 5-membered heteroaryl is selected from the group consisting of furanyl, imidazolyl, isoxazolyl, isothiazolyl, oxadiazolyl, oxazolyl, pyrazolyl, pyrrolyl, thienyl, thiazolyl, and triazolyl.

A "6-membered heteroaryl" is a 6-membered, monocyclic, aromatic ring radial having from 4 to 5 carbon atoms and from 1 or 2 heteroatoms selected from the group consisting of: 1 N; and 2 N. In certain embodiments, a 6-membered heteroaryl is selected from the group consisting of pyridinyl, pyrimidinyl, pyridazinyl, and pyrazinyl.

DETAILED DESCRIPTION OF THE INVENTION

Preparation of Compounds

General synthetic schemes for preparing compounds of formula I are set forth below.

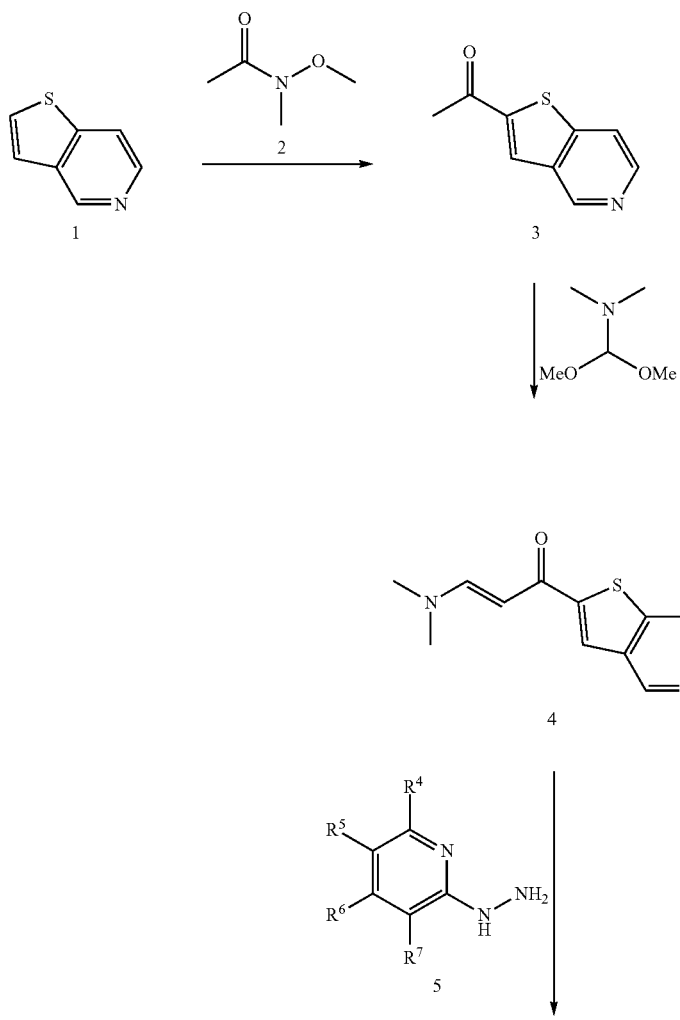

Scheme 1

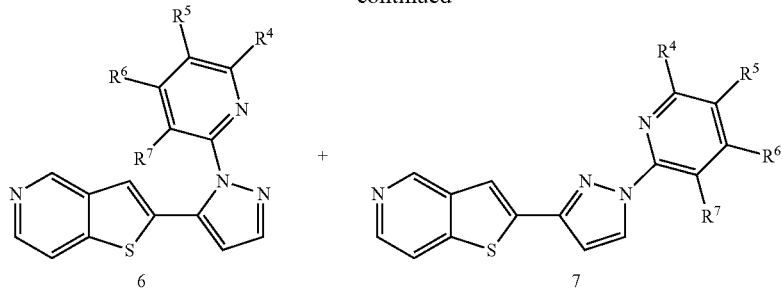

Scheme 1 depicts the synthesis of a pyrazole 6. A thieno [3,2-c]pyridine 1 (see e.g., Wikel et al. (1993) J. Het. Chem., 30: 289-290) in an aprotic solvent, such as THF (tetrahydrofuran), diethylether, etc. may be reacted with an alkyllithium reagent such as n-butyllithium at or below about −40° C. The thieno[3,2-c]pyridine is shown as unsubstituted in Scheme 1, however it may be optionally substituted as described herein. Then N-methyl-N-methoxyacetamide 2 (or other suitable acylating agents such as N-acetyl-morpholine, acetic anhydride, and acetyl chloride) is added to the reaction and the reaction is allowed to proceed at −30 to −45° C. to provide the ketone 3 (e.g., 1-(thieno[3,2-c]pyridin-2-yl)ethanone).

The ketone 3 is then reacted with dimethoxy-N,N-dimethylmethanamine ("DMF-DMA") in DMF (dimethylformamide) at about 70° C. to provide 4 (e.g., (E)-3-(dimethylamino)-1-(thieno[3,2-c]pyridin-2-yl)prop-2-en-1-one). 4 is treated with a pyridinyl-hydrazine 5 (e.g., 1-(6-methylpyridin-2-yl)hydrazine) in acetic acid at about 80° C. to yield the regioisomers 6 and 7. The regioisomer 7 can be separated from 6 to provide 6 using conventional purification techniques such as precipitation, filtration, and column chromatography.

Scheme 2

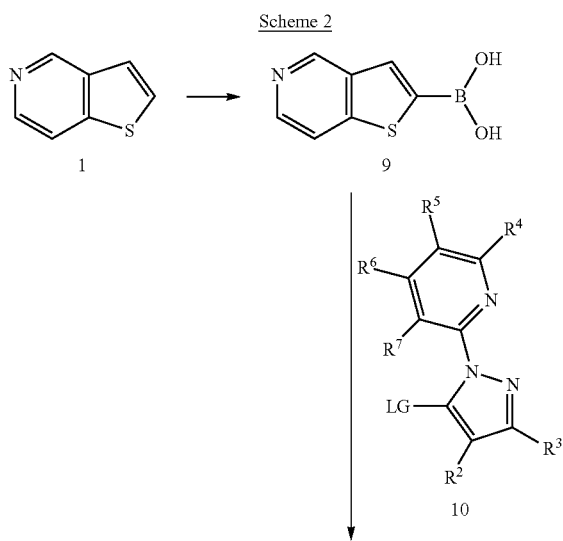

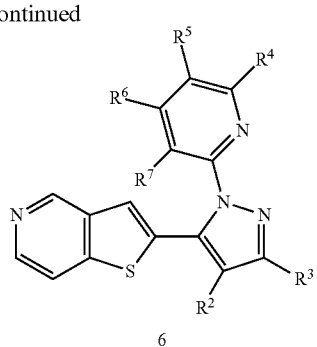

Scheme 2 depicts an alternate synthetic route to the pyrazole 6. A solution of a thieno[3,2-c]pyridine 1 may be reacted under a nitrogen gas atmosphere, in a solvent such as THF at about −50° C. to −78° C. with an alkyllithium reagent such as n-butyllithium. The thieno[3,2-c]pyridine is shown as unsubstituted in Scheme 2, however it may be optionally substituted as described herein. The addition of triisopropyl borate and phosphoric acid yields the phosphoric acid salt of the boronic acid 9. The boronate 9 is then coupled to the pyridinyl-pyrazole 10 to provide the pyrazole 6, by the addition of a base such as an inorganic carbonate base (e.g., $Na_2CO_3$, $K_2CO_3$, $NaHCO_3$, etc.) or potassium phosphate tribasic, and a palladium catalyst such as $Pd(Cl_2)$ dppf (dichloro (1,1 bis(diphenylphosphino) ferrocene) palladium(11)) and dppf [(1,1 bis(diphenylphosphino) ferrocene. The reaction may be carried out by refluxing for 1-24 hours in a suitable solvent such as THF or 1,2-dimethoxyethane; or at about 80-100° C. in dioxane. This reaction may also be carried out in the presence of KF and water. The corresponding boronate esters may be used in place of the boronic acid 9. The group LG of 10 represents a suitable leaving group such as trifluoromethanesulfonyl, Br, I, or Cl. The corresponding thieno[3,2-b]pyridin-2-yl, thieno[2,3-c] pyridin-2-yl, and thieno[2,3-b]pyridin-2-yl analogs of 6 may be prepared using thieno[3,2-b]pyridine, thieno[2,3-c]pyridine, and thieno[2,3-b]pyridine, respectively, in place of 1.

Pharmaceutically Acceptable Salts

The compounds of the present invention (e.g., compounds of Formula I) may be capable of forming pharmaceutically acceptable salts, including but not limited to acid addition and/or base salts. Pharmaceutically acceptable salts of the compounds of formula (I) include the acid addition and base salts (including disalts) thereof. Examples of suitable salts can be found for example in Stahl and Wermuth, *Handbook of Pharmaceutical Salts: Properties, Selection, and Use*, Wiley-VCH, Weinheim, Germany (2002); and Berge et al., "Pharmaceutical Salts," *J. of Pharmaceutical Science*, 1977; 66: 1-19.

Pharmaceutically acceptable acid addition salts of the compounds of Formula I include non-toxic salts derived from inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include the acetate, aspartate, benzoate, besylate (benzenesulfonate), bicarbonate/carbonate, bisulfate, caprylate, camsylate (camphor sulfonate), chlorobenzoate, citrate, edisylate (1,2-ethane disulfonate), dihydrogenphosphate, dinitrobenzoate, esylate (ethane sulfonate), fumarate, gluceptate, gluconate, glucuronate, hibenzate, hydrochloride/chloride, hydrobromide/bromide, hydroiodide/iodide, isobutyrate, monohydrogen phosphate, isethionate, D-lactate, L-lactate, malate, maleate, malonate, mandelate, mesylate (methanesulfonate), metaphosphate, methylbenzoate, methylsulfate, 2-napsylate (2-naphthalene sulfonate), nicotinate, nitrate, orotate, oxalate, palmoate, phenylacetate, phosphate, phthalate, propionate, pyrophosphate, pyrosulfate, saccharate, sebacate, stearate, suberate, succinate sulfate, sulfite, D-tartrate, L-tartrate, tosylate (toluene sulfonate), and xinafoate salts, and the like of compounds of Formula I. Also contemplated are the salts of amino acids such as arginate, gluconate, galacturonate, and the like.

Acid addition salts of the basic compounds may be prepared by contacting the free base form with a sufficient amount of the desired acid to produce a particular salt. The free base form may be regenerated by contacting the salt form with a base and isolating the free base. The free base forms may differ from their respective salt forms somewhat in certain physical properties such as solubility in polar solvents.

Pharmaceutically acceptable base addition salts may be formed with metals or amines, such as alkali and alkaline earth metal hydroxides, or of organic amines. Examples of metals used as cations are aluminum, calcium, magnesium, potassium, sodium, and the like. Examples of suitable amines include arginine, choline, chloroprocaine, N,N'-dibenzylethylenediamine, diethylamine, diethanolamine, diolamine, ethylenediamine (ethane-1,2-diamine), glycine, lysine, meglumine, N-methylglucamine, olamine, procaine (benzathine) and tromethamine.

The base addition salts of acidic compounds may be prepared by contacting the free acid form with a sufficient amount of the desired base to produce the salt in the conventional manner. The free acid form may be regenerated by contacting the salt form with an acid and isolating the free acid. The free acid forms may differ from their respective salt forms somewhat in certain physical properties such as solubility in polar solvents.

Pharmaceutical Compositions

Generally, compounds of the present invention may be administered as a pharmaceutical composition, comprising one or more pharmaceutically acceptable excipients. The phrase "pharmaceutical composition" refers to a composition suitable for administration in medical or veterinary use. The phrase "therapeutically effective amount" means an amount of a compound, or a pharmaceutically acceptable salt thereof, sufficient to inhibit, halt, or allow an improvement in the disease being treated when administered alone or in conjunction with another pharmaceutical agent or treatment in a particular subject or subject population. For example in a human or other mammal, a therapeutically effective amount can be determined experimentally in a laboratory or clinical setting, for the particular disease and subject being treated.

It should be appreciated that determination of proper dosage forms, dosage amounts and routes of administration is within the level of ordinary skill in the pharmaceutical and medical arts and is described below.

The term "excipient" is used herein to describe any ingredient other than the compound(s) of the invention. The choice of excipient typically depends to a large extent on factors such as the particular mode of administration, the effect of the excipient on solubility and stability and the nature of the dosage form. Pharmaceutically acceptable excipients are determined in part by the particular composition being administered, as well as by the particular method used to administer the composition. Accordingly, there are a wide variety of suitable formulations of pharmaceutical compositions of the present invention (see, e.g., Remington: The Science and Practice of Pharmacy, 20th ed., Gennaro at al. Eds., Lippincott Williams and Wilkins, 2000).

A compound of the present invention can be formulated as a pharmaceutical composition in the form of a syrup, an elixir, a suspension, a powder, a granule, a tablet, a capsule, a lozenge, a troche, an aqueous solution, a cream, an ointment, a lotion, a gel, an emulsion, etc.

For preparing pharmaceutical compositions from the compounds of the present invention, pharmaceutically acceptable excipients are typically solid and liquid excipients. Solid form preparations include powders, tablets, pills, capsules, cachets, suppositories and dispersible granules. A solid excipient can be one or more substances which may also act as diluents, flavoring agents, binders, preservatives, tablet disintegrating agents, or an encapsulating material.

In powders, the excipient is typically a finely divided solid which is in a mixture with the finely divided active component. In tablets, the active component is mixed with the excipient having the necessary binding properties in suitable proportions and compacted in the shape and size desired.

The powders and tablets typically contain from 1% to 95% (w/w) of the active compound. In certain embodiments, the active compound ranges from 5% to 70% (w/w). Suitable excipients are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as an excipient providing a capsule in which the active component with or without other excipients, is surrounded by a excipient, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture may then be poured into convenient sized molds, allowed to cool and thereby to solidify.

Liquid form preparations include solutions, suspensions, and emulsions, for example, water or water/propylene glycol solutions. Liquid preparations can be prepared by dissolving the active ingredient in an aqueous or non-aqueous pharmaceutically acceptable solvent, which may also contain suspending agents, sweetening agents, flavoring agents, and preservative agents as are known in the art.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents and the like.

A compound of the present invention, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane nitrogen and the like.

A topical composition according to the present invention can be in the form of solutions, lotions, salves, creams, ointments, liposomes, sprays, gels, foams, roller sticks, or any other formulation routinely used to deliver a topical pharmaceutical composition.

Formulations suitable for parenteral administration, such as, by intravenous, intramuscular, intradermal and subcutaneous routes, include aqueous and non-aqueous, isotonic sterile injection solutions, which can contain antioxidants, buffers, bacteriostats and solutes that render the formulation isotonic with the blood of the intended recipient and aqueous and nonaqueous sterile suspensions that can include suspending agents, solubilizers, thickening agents, stabilizers and preservatives.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules and powders in vials or ampules. Also, the unit dosage form can be a capsule, tablet, cachet, or lozenge itself, or it can be the appropriate number of any of these in packaged form. The formulations of compounds can be presented in unit-dose or multi-dose sealed containers, such as ampules and vials.

The compositions containing a compound of the present invention may be packaged for retail distribution (i.e., an article of manufacture). Such articles may be labeled and packaged in a manner to instruct the patient how to use the product. Such instructions may include the condition to be treated, duration of treatment, dosing schedule, etc.

The quantity of active component in a unit dose preparation may be varied or adjusted from 0.1 mg to 1000 mg, preferably 1.0 mg to 100 mg, or from 0.01% to 95% (w/w) of a unit dose, according to the particular application and the potency of the active component. The dose administered to a subject, in the context of the present invention should be sufficient to affect a beneficial therapeutic response in the subject over time. The composition can, if desired, also contain other compatible therapeutic agents.

Determination of the proper dosage for a particular situation is within the skill of the practitioner. The dose will typically be determined by the efficacy of the particular compound employed and the condition of the subject, the severity of the disease being treated, as well as the body weight or surface area of the subject to be treated. The size of the dose also will be determined by the existence, nature and extent of any adverse side-effects that accompany the administration of a particular compound in a particular subject. In determining the effective amount of the compound to be administered in the treatment or prophylaxis of the disease being treated, the physician can evaluate factors such as the circulating plasma levels of the compound, compound toxicities, and/or the progression of the disease, etc. In addition, compounds of the present invention can be administered at a rate determined by factors that can include the pharmacokinetic profile of the compound, contraindicated drugs and the side-effects of the compound at various concentrations, as applied to the mass and overall health of the subject.

Generally, treatment is initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Methods of Use

While a compound of the present invention may be most typically used to reduce scarring, the invention is not limited to this specific condition. A compound of the present invention may be used to reduce an existing scar. A compound of the present invention may also be used to alleviate any type of TGFβ-mediated condition. Examples of the TGFβ-mediated conditions include all types of cancer (e.g., breast, lung, colon, prostate, ovarian, pancreatic, melanoma, all hematological malignancies, etc.), as well as all types of fibrotic diseases (e.g., glomerulonephritis, diabetic nephropathy, hepatic fibrosis, pulmonary fibrosis, arterial hyperplasia and restenosis, scleroderma, and dermal scarring). In one particular embodiment, the TGFβ-mediated condition is dermal scarring.

The term "administering" refers to the method of contacting a compound with a subject. Thus, the compounds of the present invention can be administered by a variety of routes including injection, that is, intravenously, intramuscularly, intracutaneously, subcutaneously, intraduodenally, parentally, or intraperitoneally. Also, the compounds described herein can be administered by inhalation, for example, intranasally. Additionally, the compounds of the present invention can be administered transdermally, topically, and via implantation. In certain embodiments, the compounds of the present invention are delivered orally. The compounds can also be delivered rectally, bucally, intravaginally, or ocularly.

When administered to reduce scarring, a compound of the present invention may be typically applied to the wound and/or area around a wound. For example, a compound of the present invention can be administered topically to a wound in the form of a patch, solution, lotion, salve, cream, ointment, liposome, spray, gel, foam, roller stick, or any other formulation routinely used to deliver a topical pharmaceutical composition. Alternatively, a compound of the present invention may be administered via injection into a wound or area around a wound. In certain embodiments, a compound of the present invention is administered to a wound that has been sutured, stapled, taped, and/or bandaged, etc. In certain embodiments, a compound of the present invention is administered immediately after the wound occurs. In other embodiments, a compound of the present invention is administered within 1 hour, 8 hours, 12 hours, 1 day, 2 days, 3 days, 1 week, 2 weeks, 1 month, 6 months, 1 year, or longer than 1 year, after wound occurrence. In one particular embodiment, the wound occurs via an incision. In certain embodiments, a therapeutically effective amount of a compound of the present invention, or a pharmaceutically acceptable salt thereof may be administered to a mammal in need of such treatment to inhibit keloid scar formation. In certain embodiments, a therapeutically effective amount of a compound of the present invention, or a pharmaceutically acceptable salt thereof may be administered to a mammal in need of such treatment to inhibit hypertrophic scar formation. In certain embodiments are methods of inhibiting scar formation, comprising administering to a mammal in need of such treatment a therapeutically effective amount of a compound of formula I or a pharmaceutically acceptable salt thereof, wherein the scar would occur on the skin.

Reduction of scarring or inhibition of scar formation is meant to convey that the compounds of the present invention relate to reducing the appearance of a scar as judged by the patient or a health care practitioner (e.g., a physician). Reduction of scarring or inhibition of scar formation may be accompanied by an improvement in one or more of the following indicia, including, reduction of extracellular matrix deposition during healing, reduction of collagen deposition, reduction of size, reduction of shape, reduction of thickness, reduction of surface area, reduction of severity, reduction of height, improvement in coloration etc.

In a typical embodiment, the compound is administered topically. As used herein, topical refers to application of the compounds (and optional carrier) directly to the skin or wound area. Topical administration is especially appropriate for wounds to the skin. The dose may vary, but as a general guideline, the compound may be present in a pharmaceutically acceptable carrier in an amount of from about 0.01 to 50 w/w %, and more typically from about 0.1 to 10 w/w %. The pharmaceutical composition may be applied to the affected area from 1 to 4 times daily.

In further embodiments of the invention, the compound can be co-administered with other compounds, agents, or dressings to further enhance its activity, or to minimize potential side effects. As used in this application, co-administered refers to administering the compound of Formula I with a second medicinal, typically having a differing mechanism of action, using a dosing regimen that promotes the desired result. This can refer to simultaneous dosing, dosing at different times during a single day, or even dosing on different days. The compounds can be administered separately or can be combined into a single formulation. For the reduction of scarring, agents, compounds, or dressings may be co-administered with a compound of the present invention, including TGFβ$_3$, TGFβ$_1$ antibodies, TGFβ$_2$ antibodies, triamcinolone acetonide (9-fluoro-11,16,17-trihydroxy-17-(2-hydroxyacetyl)-10,13-dimethyl-6,7,8,9,10,11,12, 13,14,15,16,17-dodecahydrocyclopenta[a]phenanthren-3-one), steroids, corticosteroids, antibiotics, topical antibiotics, and silicone sheeting. In addition, agents, compounds, or dressings may be co-administered to a wound that improve wound healing, including 5-fluorouracil, estrogen, nACh (nicotinic acetylcholine) receptor agonists, FGF (fibroblast growth factor), EGF (epidermal growth factor), IGF (insulin-like growth factor), and PDGF (platelet-derived growth factor).

In addition, the following therapeutic agents may be co-administered with a compound of the present invention to treat a TGFβ-mediated condition. Examples of suitable therapeutic agent(s) include, but are not limited to, standard non-steroidal anti-inflammatory agents (hereinafter NSAID's) (e.g, piroxicam, diclofenac), propionic acids (e.g., naproxen, flubiprofen, fenoprofen, ketoprofen and ibuprofen), fenamates (e.g., mefenamic acid, indomethacin, sulindac, apazone), pyrazolones (e.g., phenylbutazone), salicylates (e.g., aspirin), COX-2 inhibitors (e.g., celecoxib, valdecoxib, and etoricoxib), analgesics and intraarticular therapies (e.g., corticosteroids) and hyaluronic acids (e.g., hyalgan and synvisc), anticancer agents (e.g., endostatin and angiostatin), cytotoxic drugs (e.g., adriamycin, daunomycin, cis-platinum, etoposide, taxol, taxotere), alkaloids (e.g., vincristine), and antimetabolites (e.g., methotrexate), cardiovascular agents (e.g., calcium channel blockers), lipid lowering agents (e.g., statins), fibrates, beta-blockers, ACE inhibitors, Angiotensin-2 receptor antagonists and platelet aggregation inhibitors, CNS agents (e.g., as antidepressants (such as sertraline)), anti-Parkinsonian drugs (e.g., deprenyl, L-dopa, Requip, Mirapex), MAOB inhibitors (e.g., selegine and rasagiline), comP inhibitors (e.g., Tasmar), A-2 inhibitors, dopamine reuptake inhibitors, NMDA antagonists, Nicotine agonists, Dopamine agonists and inhibitors of neuronal nitric oxide synthase), anti-Alzheimer's drugs (e.g., donepezil, tacrine, COX-2 inhibitors, propentofylline or metryfonate), osteoporosis agents (e.g., roloxifene, droloxifene, lasofoxifene or fosomax), and immunosuppressant agents (e.g., FK-506 and rapamycin).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice of the art. The following examples and biological data are being presented in order to further illustrate the invention. This disclosure should not be construed as limiting the invention in any manner.

EXAMPLES

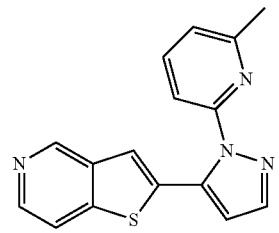 [SMILES: Cc1cccc(-n2nccc2-c2cc3cnccc3s2)n1]

Example 1

2-(1-(6-methylpyridin-2-yl)-1H-pyrazol-5-yl)thieno[3,2-c]pyridine

Step i: Thieno[3,2-c]pyridine. Thieno[3,2-c]pyridine (9.20 g; dark brown orange solid; see Wikel et al. (1993) J. Het. Chem., 30: 289-290) was dissolved in CH$_2$Cl$_2$ and subjected to column chromatography (Biotage Horizon system, 120 g Isco RediSep column, equilibrate with hexanes, elute with 45% EtOAc ("ethyl acetate")/hexanes, isocratic). The collected fractions were a pale yellow oil that concentrated in vacuo to provide 8.48 g of a solid.

Alternatively, thieno[3,2-c]pyridine was also purified as follows: thieno[3,2-c]pyridine (84.6 g) was dissolved in approximately 180 mL of dichloromethane. The solution was split into three approximately even portions. Each portion was applied to a flash silica cartridge (Analogix SuperFlash SF65-400) and was eluted with an isocratic method (45% or 50% ethyl acetate in hexanes). The desired fractions were concentrated to provide thieno[3,2-c]pyridine as a light-yellow solid. Three combined chromatographies afforded a total of 75 g of the title compound; $^1$H NMR (400 MHz, CDCl$_3$) δ 9.12 (d, 1H, J=1.0 Hz), 8.44 (d, 1H, J=5.7

Hz), 7.79 (dt, 1H, J=5.7, 1.0 Hz), 7.47 (m, 1H), 7.43 (m, 1H); MS (APCI+) m/z 136 (MH+).

Step ii: 1-(thieno[3,2-c]pyridin-2-yl)ethanone. A solution of thieno[3,2-c]pyridine (5.0 g) in 75 mL THF (tetrahydrofuran) was cooled to −45° C. in a CH$_3$CN/dry ice bath. n-Butyllithium (1.6M in hexanes) (35.0 ml) was added dropwise maintaining the internal temperature at or below −40° C. The addition took about 45 minutes. The reaction was stirred for 1 hour at −45° C. N-methyl-N-methoxyacetamide in 5 mL THF was added and as a result the reaction warmed to −30° C. The reaction was stirred at −45° C. for 1.5 hours. The reaction was quenched with saturated NH$_4$Cl. The aqueous layer had a pH of about 8. The aqueous layer was extracted three times into EtOAc. The combined organic extracts were washed with brine and dried over MgSO$_4$. The material was filtered, concentrated on a rotary evaporator and subjected to column chromatography (Biotage Horizon system, 120 g Analogix column, equilibrate with hexanes, elute with 50% EtOAc/hexanes). The most pure fractions were concentrated on a rotary evaporator and then triturated with Et$_2$O to remove some color and collect a pale orange solid by filtration (2.667 g).

Step iii: (E)-3-(dimethylamino)-1-(thieno[3,2-c]pyridin-2-yl)prop-2-en-1-one. N,N-dimethylformamide-dimethylacetal (DMF-DMA) (9.5 ml) was added to a solution of 1-(thieno[3,2-c]pyridin-2-yl)ethanone (3.17 g) in 20 mL DMF. The reaction was heated to 70° C. overnight. The reaction was then cooled to room temperature. The DMF was removed on a rotary evaporator to obtain a dark brown orange solid. The residue was diluted with EtOAc and water. A large amount of yellow solid was evident. This was collected by filtration (3.54 g). This solid was dried in a 50° C. vacuum oven.

Step iv: 2-(1-(6-methylpyridin-2-yl)-1H-pyrazol-5-yl) thieno[3,2-c]pyridine. (E)-3-(dimethylamino)-1-(thieno[3,2-c]pyridin-2-yl)prop-2-en-1-one (3.69 g) and 1-(6-methylpyridin-2-yl)hydrazine (3.3 g) (which may be synthesized as described below for Example 7, Step ii) was dissolved in 40 mL acetic acid. The reaction was heated to 80° C. for 4.5 hours. The reaction was cooled to room temperature and the solvent was removed on a rotary evaporator.

The deep orange red residue was dissolved in EtOAc and saturated NaHCO$_3$ was added until the aqueous layer was pH about 7-8 (about 250 mL). The aqueous layer was extracted four times into EtOAc. The combined organic extracts were washed with brine and dried over MgSO$_4$. The material was filtered, concentrated, and subjected to column chromatography (Biotage Horizon system, 80 g Isco RediSep column, 0-50%, hold at 50%, 50-75%, hold at 75% EtOAc/hexane).

The fractions containing the desired material were combined and concentrated. The resulting material was dissolved in hot MeOH and a precipitate formed on cooling to room temperature. After one hour at room temperature, the flask was stored at 4° C. for 3 hours. The solid was collected by filtration, rinsing with hexanes giving 2.79 g. The material was dissolved in boiling acetonitrile and allowed to cool to room temperature. Once a precipitate became evident the precipitate was collected by filtration. The precipitate was the undesired regioisomer (2-(1-(6-methylpyridin-2-yl)-1H-pyrazol-3-yl)thieno[3,2-c]pyridine). This process was repeated four times to enrich the acetonitrile filtrate with desired regioisomer (2-(1-(6-methylpyridin-2-yl)-1H-pyrazol-5-yl)thieno[3,2-c]pyridine). The acetonitrile filtrate on cooling contained a white precipitate that was the desired product. A total yield of 1.21 g of desired product was obtained (2-(1-(6-methylpyridin-2-yl)-1H-pyrazol-5-yl) thieno[3,2-c]pyridine).

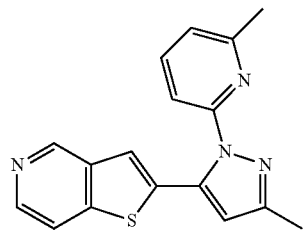 [SMILES: Cc1cccc(-n2nc(C)cc2-c2cc3cnccc3s2)n1]

Example 2

2-[3-methyl-1-(6-methylpyridin-2-yl)-1H-pyrazol-5-yl]thieno[3,2-c]pyridine

Step i: Thieno[3,2-c]pyridin-2-yl boronic acid. A three neck flask fitted with an internal thermometer containing thieno[3,2-c]pyridine (5.0 g, 37 mmol, 1 equivalent) was evacuated and then filled with a nitrogen gas atmosphere. THF (60 mL) was added and the solution was cooled to −44° C. (CH$_3$CN/dry ice). n-Butyllithium (1.6M/hexane, 25 mL, 41 mmol, 1.1 equivalents) was added over 10 minutes, while maintaining the internal temperature at or below −33° C. The reaction was stirred at −33 to −45° C. for 60 minutes. Triisopropyl borate (10.2 mL, 44 mmol, 1.2 equivalents) was added and the cooling bath removed. The reaction was allowed to proceed for 105 minutes. Then 3.0 mL phosphoric acid (85% aqueous, 3.0 mL, 44 mmol, 1.2 equivalents) was added. A yellow solid formed, which was diluted with water and Et$_2$O (about 150 mL each). A yellow solid was collected by filtration and was dried by suction overnight (5.05 g). Analytical Data: $^1$H NMR (400 MHz, METHANOL-d$_4$) δ ppm 7.95 (1 H, s), 8.09 (1 H, d, J=5.9 Hz), 8.34 (1 H, d, J=6.1 Hz), 9.09 (1 H, s). MS (APCI, M+1) 180.1. Microanalysis for C$_7$H$_6$BNSO$_2$.H$_3$PO$_4$: calculated C, 30.35; H, 3.27; N, 5.06; P, 11.18. Found: C, 41.12; H, 3.19; N, 6.53; P, 0.68%.

Step ii. 3-methyl-1-(6-methylpyridin-2-yl)-1H-pyrazol-5-ol. Ethyl acetoacetate (10 mL, 78 mmol) and (6-methylpyridin-2-yl)-hydrazine (10.1 g, 82 mmol) were combined in 100 mL acetic acid. The reaction was heated to 80° C. for 4 hours and 15 minutes. The reaction was cooled to room temperature. The solvent was removed on a rotary evaporator to provide a dark residue, which was dissolved in EtOAc. The solution was washed twice with saturated NaHCO$_3$, then once with water, and then once with brine. A reddish brown solid became evident in the biphasic mixture. The biphasic mixture was filtered, collecting the solid. The solid was washed with Et$_2$O to provide a first solid (6.02 g). The layers of the filtrate were separated using a separatory funnel. The organic layer was dried over MgSO$_4$. The material was filtered and concentrated by rotary evaporation. The resulting brown solid was triturated with Et$_2$O and subjected to filtration to provide a second solid (1.98 g) and a first filtrate. A solid precipitated out of the first filtrate, which was collected by pouring the filtrate into another filter to provide 1.69 g of a third solid. The first filtrate and the 1.98 g (second solid) were concentrated to dryness. The resulting solid was dissolve in hot EtOAc and hexanes were added until a cloudiness persisted. The solution was allowed to stand overnight. A very dark solid was isolated by filtration and subjected to column chromatography (Biotage Horizon system, 35 g Analogix column, 30% EtOAc/hexane). A yellow solid was isolated that was dissolved in hot EtOAc and hexanes were added until a cloudiness persisted. The solution was allowed to stand overnight. The mother liquor was decanted and the solid was dried solid in 50° C. vacuum oven for several hours to provide a fourth solid. The first solid (6.02 g), third solid (1.69 g), and fourth solid (4.03 g) were combined to provide 11.74 g of the title compound.

Step iii. 3-methyl-1-(6-methylpyridin-2-yl)-1H-pyrazol-5-yl trifluoromethanesulfonate. A mixture of 3-methyl-1-(6-methylpyridin-2-yl)-1H-pyrazol-5-ol (10.0 g in CH$_2$Cl$_2$ (100 mL) and Et$_3$N (triethylamine) (8.1 mL) was cooled at −70° C.

Triflic anhydride (9.8 mL) was added over 10 minutes while maintaining the temperature below −50° C. The reaction suspension was warmed to room temperature and became a solution. The solution was concentrated to remove most of the CH$_2$Cl$_2$. The solution was loaded directly onto an Analogix SuperFlash SF65-400; using a Biotage auto fraction collector; EtOAc/hexanes (20/80). Fractions containing a colorless liquid were isolated (9.46 g).

Step iv: 2-[3-methyl-1-(6-methylpyridin-2-yl)-1H-pyrazol-5-yl]thieno[3,2-c]pyridine. In a 100 mL three neck round bottom flask fitted with a reflux condenser was added 3-methyl-1-(6-methylpyridin-2-yl)-1H-pyrazol-5-yl trifluoromethanesulfonate (1.16 g), thieno[3,2-c]pyridine-2-ylboronic acid (1.0 g), potassium phosphate tribasic (2.3 g) and 30 mL dioxane. The flask was evacuated under a vacuum and the suspension bubbled with nitrogen gas. To this was added PdCl$_2$(dppf) (Strem, dichloro[1,1'-bis(diphenylphosphino)ferrocene]palladium (II) dichloromethane adduct, 0.60 g). Again the flask was evacuated under a vacuum and the suspension bubbled with nitrogen gas. The reaction was heated to 100° C. and permitted to run overnight. The reaction was cooled to room temperature and filtered through a pad of Celite, eluting with EtOAc (~600 mL). The EtOAc filtrate was concentrated to dryness on rotary evaporator. The residue was diluted with CH$_2$Cl$_2$ and a beige solid was filtered off. The CH$_2$Cl$_2$ filtrate was purified by column chromatography (Biotage Horizon system, 34 g Analogix column, 0-100% EtOAc/hep, hold at 100% EtOAc followed by 10% MeOH/EtOAc). The fractions containing desired product were combined and concentrated on the rotary evaporator to give a dark oil.

The dark oil (about 800 mg) was subjected to preparative column chromatography on a Phenomenex, Gemini C-18 column (150×19 mm, 5 □M; Mobile Phase A: Water (+0.1% NH$_4$OH), B: CH$_3$CN (+0.1% NH$_4$OH); Gradient: 90-10% A over 10 min, hold at 90% A for 1.5 minutes; Flow Rate: 28 mL/min; Injection Volume: 2 mL; Detection: DAD 210-350 nm, MS APCI$^+$, MS APCI$^-$).

The desired fractions were dried down in a rotary evaporator. The solid was dissolved in hot EtOH and then 2-5 mLs of heptane was added. After standing, the material was filtered.

The filtrate was concentrated to dryness. Diethylether was added and the solution was filtered on a sintered glass funnel. Additional diethylether was used to wash the material until <10 mg of brown solid remained on the sintered glass funnel. The filtrate was concentrated to dryness giving an off-white solid.

The off-white solid was dissolved in hot EtOH (about 1-2 mL) and diluted with heptane until a cloudiness persisted, and was permitted to stand. Needles (slight yellow color) then started to precipitate from the solution. After about 3 hours, the mother liquors were decanted into another flask.

The needles were dried in a 40° C. vacuum oven for over 48 hours to provide 65 mg of a white solid. mp 131-132° C.

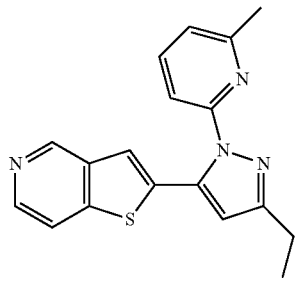 [SMILES: CCc1cc(-c2cc3cnccc3s2)n(-c2cccc(C)n2)n1]

Example 3

2-[3-ethyl-1-(6-methylpyridin-2-yl)-1H-pyrazol-5-yl]thieno[3,2-c]pyridine

Step i: 5-ethyl-2-(6-methyl-pyridin-2-yl)-2H-pyrazol-3-ol. A stirring mixture of 6-methyl-pyridin-2-yl)-hydrazine (10.0 g) and ethyl propionylacetate (12 mL) in glacial acetic acid (100 mL) was warmed to 80° C. for five hours. The reaction mixture was concentrated under reduced pressure and the evaporate was treated with saturated aqueous sodium bicarbonate (200 mL). The mixture was extracted with ethyl acetate (200 mL). The organic phase was washed with a fresh portion of saturated aqueous sodium bicarbonate (200 mL), water (200 mL), and brine solution (200 mL). The organic phase was subsequently dried over anhydrous sodium sulfate and was concentrated under reduced pressure. The evaporate was purified by flash silica gel column chromatography. Elution through a silica cartridge (Analogix, 400 g) with a gradient (100% hexanes to 60% ethyl acetate in hexanes) afforded an oil. The oil was reconstituted in chloroform and the solution was concentrated under reduced pressure to afford the title compound as an oil (7.2 g); $^1$H NMR (400 MHz, CDCl$_3$) δ 13.07 (broad s, 1H), 7.70 (m, 1H), 7.64 (d, 1H, J=8.2 Hz), 6.92 (d, 1H, J=7.4 Hz), 5.42 (s, 1H), 2.59 (quartet, 2H, J=7.6 Hz), 2.51 (s, 3H), 1.24 (t, 3H, J=7.6 Hz); $^{13}$C NMR (100 MHz, CDCl$_3$) δ 13.5, 22.7, 23.8, 86.8, 108.8, 119.2, 140.2, 154.3, 155.0, 157.2, 157.4; MS (APCI$^+$) 204 (MH$^+$).

Step ii: trifluoro-methanesulfonic acid 5-ethyl-2-(6-methyl-pyridin-2-yl)-2H-pyrazol-3-yl ester. To a stirring mixture of 5-ethyl-2-(6-methyl-pyridin-2-yl)-2H-pyrazol-3-ol (7.1 g) and triethylamine (5.4 mL) in dichloromethane (75 mL) at −78° C. under a nitrogen atmosphere was added trifluoromethanesulfonic anhydride (6.5 mL) over 5 minutes. The cold bath was removed and the reaction mixture was allowed to warm to room temperature and was stirred overnight. The reaction mixture was concentrated under reduced pressure and the concentrate was purified by flash silica gel column chromatography. Elution through a silica cartridge (Analogix SuperFlash SF65-400) with a gradient (100% hexanes to 35% ethyl acetate in hexanes over 2400 mL) afforded the title compound as an oil (10.38 g) after chloroform chase; $^1$H NMR (400 MHz, CDCl$_3$) δ 7.69 (m, 1H), 7.59 (dd, 1H, J=8.2, 0.6 Hz), 7.07 (dd, 1H, J=7.6, 0.4 Hz), 6.10 (s, 1H), 2.68 (quartet, 2H, J=7.6 Hz), 2.57 (s, 3H), 1.28 (t, 3H, J=7.6 Hz); $^{19}$F NMR (376 MHz, CDCl$_3$) δ −73.9 (s); MS (APCI$^+$) 336 (MH$^+$), 204 (MH$^+$-SO$_2$CF$_3$).

Step iii: 2-[3-ethyl-1-(6-methylpyridin-2-yl)-1H-pyrazol-5-yl]thieno[3,2-c]pyridine. In a 100 mL three neck round bottom flask fitted with a reflux condenser was added 3-ethyl-1-(6-methylpyridin-2-yl)-1H-pyrazol-5-yl trifluoromethanesulfonate (1.21 g), thieno[3,2-c]pyridin-2-ylboronic acid (1.0 g), potassium phosphate tribasic (2.3 g) and 30 mL dioxane. The flask was evacuated under a vacuum and the suspension bubbled with nitrogen gas. To this was added $PdCl_2$(dppf) (Strem, dichloro[1,1'-bis(diphenylphosphino)ferrocene]palladium (II) dichloromethane adduct, 0.60 g). Again the flask was evacuated under a vacuum and the suspension bubbled with nitrogen gas. The reaction was heated to 100° C. and allowed to proceed overnight. The reaction was cooled to room temperature. The reaction was then filtered through Celite, rinsing well with EtOAc. The filtrate was concentrated on a rotary evaporator and the dark oily material was diluted with $CH_2Cl_2$. An off-white solid was filtered from the $CH_2Cl_2$. The filtrate was loaded on a column (Biotage Horizon system, 34 g Analogix column, 0-100% hepane/EtOAc), then holding at 100% EtOAc). The desired fractions were collected to yield a dark oil (about 900 mg). The fractions were chromatographed on a Phenomenex, Gemini C-18 column as described above in Example 2.

The desired fractions were combined and dried down in a rotary evaporator to provide a solid sample. The solid sample was dissolved in warm EtOH. The solution was concentrated to dryness on a rotary evaporator to obtain a dark residue. The residue was dried in 45° C. vacuum oven for 2 hours. The resulting material was part dark oil and part solid. Diethylether was added and the material was filtered to provide a dark brown solid, and a light orange-yellow colored filtrate. The filtrate was concentrated to dryness to obtain a tan solid (231 mg).

Diethylether was added to the tan solid. The material was filtered through fluted filter paper, leaving a brown residue on filter paper. The filtrate was concentrated to dryness on the rotary evaporator. The resulting solids were again dissolved in hot EtOH (1-2 mL) and diluted with heptane until a cloudiness persisted. After 2 hours of standing, no precipitate was evident. The liquid was then concentrated to dryness. While on a rotary evaporator, when the liquid had reduced to approximately half of the original volume, a brown solid was evident. The liquid was removed from the rotary evaporator and the solution began to display a white cloudiness. The liquid was filtered into another flask using filter paper to remove brown solid. A white solid started to precipitate in the filtrate. After about 15 minutes, no more precipitation was observed, and the material was filtered to obtain a solid. The solid was dried in a 40° C. vacuum oven for about 48 hours to provide 71 mg. mp 89-90° C.

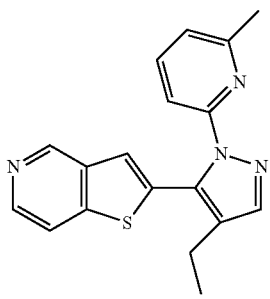 [SMILES: CCc1cnn(-c2cccc(C)n2)c1-c1cc2cnccc2s1]

Example 4

2-[4-ethyl-1-(6-methylpyridin-2-yl)-1H-pyrazol-5-yl]thieno[3,2-c]pyridine

Step i: 4-ethyl-1-(6-methylpyridin-2-yl)-1H-pyrazol-5-ol. A suspension of KOMe (14.0 g) and ethyl butyrate (19.8 mL) in DMF (15 mL) was stirred at room temperature. Ethyl formate (8.1 mL) was added over 15 minutes, which resulted in much foaming. The reaction was stirred for an additional hour, and the reaction became a very stirrable mixture with no foamy layer. A solution of 1-(6-methylpyridin-2-yl)hydrazine (12.3 g), MeOH (35 mL), and HOAc (5.7 mL) were added over 20 minutes. The reaction was exothermic and reached a temperature of 30° C. after an initial addition. An ice-water bath was used to keep the reaction below 20° C. for the remaining addition of the solution. The reaction was heated at reflux for 3 hours and then stirred at room temperature for about 48 hours.

The reaction was cooled to 10° C. with an ice-water bath. The pH was adjusted to about 7 with HOAc (10 mL) to obtain a thick, unstirrable mass. The reaction was diluted with $H_2O$ (100 mL) to result in a dark red solution. The solution was extracted with EtOAc (200 mL). The organic phase was washed with $H_2O$ (2×100 mL), dried ($MgSO_4$) and $SiO_2$ (30 mL), and filtered through $SiO_2$ (30 mL). The material was concentrated to provide 10.50 g of a dark brown oil. The oil was chromatographed using an Analogix SuperFlash SF65-400 and Biotage auto fraction collector; EtOAc/hexanes (40/60). Fractions containing the desired product were combined to afford 6.40 g of a yellow-orange liquid.

Step ii: 4-ethyl-11-(6-methylpyridin-2-yl)-1H-pyrazol-5-yl trifluoromethanesulfonate. A solution of 4-ethyl-1-(6-methylpyridin-2-yl)-1H-pyrazol-5-ol (6.40 g) in $CH_2Cl_2$ (65 mL) and $Et_3N$ (4.8 mL) was cooled at −70° C. Triflic anhydride ($Tf_2O$) (5.83 mL) was added over 10 minutes while maintaining the temperature below −50° C. The reaction is exothermic. The reaction was stirred for an additional 30 minutes at less than −50° C. and then warmed to room temperature. The reaction was then cooled at to less than −50° C. and an additional portion of $Tf_2O$ (1.1 mL; 20%) and $Et_3N$ (1.0 mL; 20%) was added. After an hour incubation, then reaction was concentrated to remove most of the $CH_2Cl_2$. The reaction was loaded directly onto an Analogix SuperFlash SF40-150; using a Horizon auto fraction collector; EtOAc/heptane (20/80). The column was washed with EtOAc/heptane (30/70). Fractions containing the desired product were collected to provide 6.98 g as a pale yellow liquid.

Step iii: 2-[4-ethyl-1-(6-methylpyridin-2-yl)-1H-pyrazol-5-yl]thieno[3,2-c]pyridine. In a 100 mL three neck round bottom flask fitted with a reflux condenser was added 4-ethyl-1-(6-methylpyridin-2-yl)-1H-pyrazol-5-yl trifluoromethanesulfonate (1.2 g), thieno[3,2-c]pyridin-2-ylboronic acid (1.2 g), potassium phosphate tribasic (2.3 g) and 30 mL dioxane. The flask was evacuated under a vacuum and the suspension bubbled with nitrogen gas. To this was added $PdCl_2$(dppf) (Strem, Dichloro[1,1'-bis(diphenylphosphino)ferrocene]palladium (II) dichloromethane adduct, 0.60 g). Again the flask was evacuated under a vacuum and the suspension bubbled with nitrogen gas. The reaction was heated to 100° C. overnight. Then 0.295 g $PdCl_2$(dppf) (Strem, Dichloro[1,1'-bis(diphenylphosphino)ferrocene]palladium (II) dichloromethane adduct) was added and the reaction was continued for 4 hours and 15 minutes. The reaction was cooled to room temperature.

The reaction contents were filtered through Celite rinsing well with EtOAc until the desired product had eluted. The filtrate was concentrated to dryness on a rotary evaporator to form a dark residue. The dark residue was taken up in CH₂Cl₂ and the solids were filtered away. The resulting filtrate was reduced by concentration on a rotary evaporator before loading the material on a column (Biotage Horizon system, 0-100% EtOAc over 700 mL then hold at 100% EtOAc, 500 mL). The tubes with most product evident had a white solid on the sides of the flask.

The tubes containing desired product were concentrated by rotary evaporation to afford a dark oil. The dark oil was triturated with Et₂O and the solid was filtered away. Additional solid precipitate was isolated from the filtrate and combined with the solid from the original filtration. The combined solids were dissolved in hot EtOH (about 2 mL). Heptane was added until a precipitate started to form. A dark solid then formed. After about 10 minutes, it appeared that the solid had finished precipitating. The mixture was filtered through paper filter into another flask. The filtrate was diluted with more heptane until a cloudiness persisted. The filtrate was allowed to stand overnight at room temperature. White needles formed in the flask with a dark residue on the bottom of flask. The contents of the flask were concentrated to dryness on a rotary evaporator and dissolved in 1-2 mL hot EtOH, filtered through filter paper and diluted with heptane until a cloudiness persisted. The flask was allowed to stand for 2 hours. Then the mixture was put on a rotary evaporator to reduce the volume of the material. While on the rotary evaporator, when approximately half of the original volume was present, a brown solid became evident. The flask was removed from the rotary evaporator and filtered into another flask using filter paper to remove a brown solid. A white solid started to precipitate in the filtrate. The white solid was collected by filtration and dried in a 40° C. vacuum oven for over 48 hours to obtain 85 mg of the title compound.

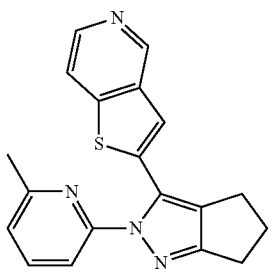 [SMILES: Cc1cccc(-n2nc3c(c2-c2cc4cnccc4s2)CCC3)n1]

Example 5

2-(2-(6-methylpyridin-2-yl)-2,4,5,6-tetrahydrocyclopenta[c]pyrazol-3-yl)thieno[3,2-c]pyridine Step i: thieno[3,2-c]pyridine-2-boronic acid. To a stirring mixture consisting of thieno[3,2-c]pyridine (2.0 g) in anhydrous tetrahydrofuran (25 mL) at −40° C. was added a solution consisting of 1.6 M n-butyllithium in hexanes (10 mL) over several minutes (dropwise at first followed by a slow, steady stream). The reaction mixture was stirred for five minutes and triisopropyl borate (4.2 mL) was subsequently added. The cold bath was removed and the mixture was allowed to stir for one hour. Water (2 mL) was added to the stirring mixture, which caused a pale yellow solid to precipitate instantly. The precipitate was collected by vacuum filtration and the solids were rinsed lightly with water (giving a cloudy yellow filtrate) and subsequently with diethyl ether (giving a dark orange filtrate). The aqueous portion of the filtrate was separated from the organic solvent, and then diluted with 1,4-dioxane (100 mL) and the solution was concentrated under reduced pressure. Addition of 1,4-dioxane (100 mL) to the concentrate and subsequent concentration under reduced pressure was repeated twice to afford a yellow powder (0.8 g) upon final evaporation.

Step ii: 2-[(6-methyl-pyridin-2-yl)-hydrazono]-cyclopentanecarboxylic acid ethyl ester. A solution of ethyl 2-oxo-cyclopentanecarboxylate (6.34 g, 5.88 mL) and (6-methyl-pyridin-2-yl)-hydrazine (5 g) in ethanol (100 mL) was heated to 80° C. under an atmosphere of nitrogen for about 19 hours. The reaction mixture was cooled to room temperature and the solvent removed in vacuo to provide a crude material (7.72 g), which was directly taken to the next reaction.

Step iii: 2-(6-methyl-pyridin-2-yl)-2,4,5,6-tetrahydro-cyclopentapyrazol-3-ol. A solution of crude 2-[(6-methyl-pyridin-2-yl)-hydrazono]-cyclopentanecarboxylic acid ethyl ester (6.6 g) and sodium methoxide (2.73 g) in methanol (250 mL) was concentrated under reduced pressure, nearly to dryness, to provide a brown paste. This paste was then heated to 160° C. for 2 hours being cautious of excessive bubbling. After 2 hours the reaction was cooled to room temperature and water (100 mL) was added. The pH was adjusted to 7 with 1N HCl, ethyl acetate (200 mL) was then added and the resultant mixture was stirred until precipitate dissolution occurred. The layers were separated and the aqueous layer was washed with another portion of ethyl acetate (100 mL). The combined organic layers were washed with water (200 mL) and brine (200 mL) and dried over MgSO₄, filtered, and concentrated in vacuo to provide of product (3.6 g) to use without any further purification.

Alternatively: The same reaction can be carried out at a lower temperature of 125° C. by starting with 21.0 g of 2-[(6-methyl-pyridin-2-yl)-hydrazono]-cyclopentanecarboxylic acid ethyl ester to provide 17.3 g of crude product.

Step iv: trifluoro-methanesulfonic acid 2-(6-methyl-pyridin-2-yl)-2,4,5,6-tetrahydro-cyclopentapyrazol-3-yl ester. To an oven-dried rounded bottomed flask was added 2-(6-methyl-pyridin-2-yl)-2,4,5,6-tetrahydro-cyclopentapyrazol-3-ol (17.3 g) and triethylamine (9.76 g, 13.44 mL) in dichloromethane (350 mL) and the reaction mixture was cooled to −78° C. To this was added trifluoromethane sulfonic anhydride (16.23 mL) via a pressure equalizing funnel over 10 minutes. The resultant mixture was stirred at −78° C. for 1 hour and then allowed to warm to room temperature and stir for an additional hour. The solvent was removed in vacuo to provide a brown precipitate. The brown precipitate was purified via flash silica gel chromatography (60% hexanes/40% ethyl acetate) to provide an off-white solid (8.848 g) followed by another batch of material (12.2 g) of slightly less pure material.

Step iv: 2-(2-(6-methylpyridin-2-yl)-2,4,5,6-tetrahydrocyclopenta[c]pyrazol-3-yl)thieno[3,2-c]pyridine. An oven-dried three-neck round-bottom flask equipped with reflux condenser and gas inlet valve was charged with thieno[3,2-c]pyridine-2-boronic acid (0.7 g). The flask was evacuated and purged with nitrogen gas three times. The content of the flask was kept under a nitrogen atmosphere for four days. To the reaction flask was added trifluoro-methanesulfonic acid 2-(6-methyl-pyridin-2-yl)-2,4,5,6-tetrahydro-cyclopentapyrazol-3-ylester (0.7 g), potassium phosphate tribasic (2.5 g), and 1,4-dioxane (30 mL). The flask was evacuated and purged with nitrogen three times more. Dichloro[1,1'-bis(diphenylphosphino)ferrocene]palladium (II) dichloromethane adduct (0.65 g) and 1,1'-bis(diphenylphosphino)ferrocene (0.43 g) were added and the mixture was degassed and purged with nitrogen three more times. The stirring mixture was brought to reflux overnight. The reaction mixture was diluted with ethyl acetate (250 mL) and the solution was treated with activated carbon and filtered through Celite.

The resulting filtrate was concentrated under reduced pressure and the concentrate was purified on a 120 g RediSep flash silica cartridge on the Biotage system with 100% hexanes to 100% ethyl acetate over 1800 mL followed by 100% ethyl acetate until the desired material eluted. The desired material was a dark residue. A dark liquid separated from a solid that adhered to the insides of the flask. The liquid was removed with absolute ethanol by drawing off with a pipet and the dark solution was evaporated overnight to a dark viscous residue. The material was dissolved in acetonitrile (15 mL) and was purified by prep HPLC (Waters prep HPLC system; Stationary phase: Waters DeltPak C18 5 □m, 100 Angstom, 300×50 mm I.D., P/N 011801, WAT 011801, No. 330009125W; Mobile phase 80:20 to 40:60 water-acetonitrile with 0.1% formic acid over 30 minutes). The combined fractions were combined and concentrated under reduced pressure to give a clear colorless aqueous solution. The solution was treated with saturated aqueous potassium carbonate to give a milky suspension. Extraction with one portion of diethyl ether and two portions of ethyl acetate, drying of the combined extracts over anhydrous potassium carbonate, and concentration under reduced pressure gave a film that began to solidify with time. The film was dissolved in absolute ethanol and was concentrated under reduced pressure to afford a light-yellow oil that solidified with time. The material was subjected to high vacuum at room temperature to afford the title compound as a light-yellow solid (21 mg); melting point: solid form morphs from 121-126° C., melts at 146-148° C.

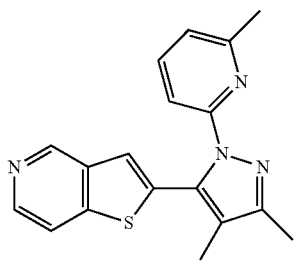 [SMILES: Cc1cccc(-n2nc(C)c(C)c2-c2cc3cnccc3s2)n1]

Example 6

2-[3,4-dimethyl-1-(6-methylpyridin-2-yl)-1H-pyrazol-5-yl]thieno[3,2-c]pyridine

Step I. 3,4-dimethyl-1-(6-methylpyridin-2-yl)-1H-pyrazol-5-ol. To a 250 mL round-bottomed flask were added ethyl 2-methyl acetoacetate (5.0 g, 35 mmol), 1-(6-methylpyridin-2-yl)hydrazine (4.48 g, 36 mmol), and 12 mL acetic acid. The mixture was heated at 80° C. for 9 hours. Water and EtOAc were added to the mixture. The layers were separated. The aqueous layer was extracted with EtOAc. The combined organic layers were washed with water and brine, dried (MgSO$_4$), filtered and concentrated in vacuo (6.68 g).

Step ii. 3,4-dimethyl-1-(6-methylpyridin-2-yl)-1H-pyrazol-6-yl trifluoromethanesulfonate. To the 500 mL round-bottomed flask with 3,4-dimethyl-1-(6-methylpyridin-2-yl)-1H-pyrazol-5-ol (6.68 g, 33 mmol) were added Et$_3$N (5.5 mL, 39 mmol) and 35 mL CH$_2$Cl$_2$. the solution was cooled in dry ice acetone bath. Tf$_2$O (6.1 mL, 36 mmol) was added slowly. The mixture was stirred at −78° C. and allowed to warm to room temperature. The mixture was then concentrated in vacuo. The crude product was purified using a Biotage Horizon System (0 to 25% EtOAc/hexane) to afford a colorless oil (8.28 g).

Step iii: 2-[3,4-dimethyl-1-(6-methylpyridin-2-yl)-1H-pyrazol-6-yl]thieno[3,2-c]pyridine. In a 100 mL three neck round bottom flask fitted with a reflux condenser was added 3,4-dimethyl-1-(6-methylpyridin-2-yl)-1H-pyrazol-5-yl trifluoromethanesulfonate (0.90 g, 2.7 mmol, 1.2 equivalents), thieno[3,2-c]pyridin-2-ylboronic acid trihydrogen phosphate (0.72 g, 2.6 mmol, 1 equivalent), potassium phosphate tribasic and 20 mL dioxane. The flask was evacuated under a vacuum and the suspension bubbled with nitrogen gas. To this was added PdCl$_2$(dppf) (Strem, Dichloro[1,1'-bis(diphenylphosphino)ferrocene]palladium (II) dichloromethane adduct, 0.54 g, 0.65 mmol, 0.3 equivalents). Again the flask was evacuated under a vacuum and the suspension bubbled with nitrogen gas. The reaction was heated to 100° C. for 16 hours and then cooled to room temperature.

The reaction was filtered through Celite, rinsing well with EtOAc until all the desired material eluted (about 400 mL). The EtOAc filtrate was concentrated to a dark residue. The dark residue was taken up in CH$_2$Cl$_2$ and the solids were filtered off. The CH$_2$Cl$_2$ was subjected to column chromatography (Biotage Horizon system, 0-100% hepane/EtOAc over 800 mL then hold at 100% EtOAc, 500 mL). The fractions were concentrated into 3 portions: the portion that contained a lightly colored oil (420 mg) partially solidified after standing overnight. The material was dissolved in hot EtOH and heptane was added. Upon standing overnight no solid appeared to precipitate. The material was concentrated to dryness. About 15 mL of Et$_2$O was added and the material was filtered through a paper filter, leaving a minor amount of a tan residue. The residue was concentrated to dryness and about 1 mL Et$_2$O was added. Then about 15 mL heptane was added until the mixture remained cloudy. A precipitate was not apparent after standing at 4° C. for about 2 hours. The material was then concentrated to dryness to obtain a brown oil. Hepatane was added and small circles of solid formed, some were off-white, others were brown. The heptane was decanted and the solid was dried in a 50° C. vacuum oven for about 48 hours to provide 229 mg of a tan solid. mp 108-109° C.

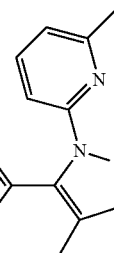

Example 7

2-[4-Methyl-2-(6-methyl-pyridin-2-yl)-2H-pyrazol-3-yl]-thieno[3,2-c]pyridine

Step i: Thieno[3,2-c]pyridine 2-boronic acid trihydrogen phosphate. To a stirring mixture of thieno[3,2-c]pyridine (2.0 g) in anhydrous tetrahydrofuran (25 mL) at −40° C. was added a solution of 1.6 M n-butyllithium in hexanes (10 mL) dropwise over five minutes. The reaction mixture was stirred for ten minutes and triisopropyl borate (4.2 mL) was subsequently added. The cold bath was removed and the mixture was allowed to stir for three hours. Phosphoric acid (85% aqueous solution, 1.2 mL) was added to the stirring mixture. Water (10 mL) was subsequently added, which caused a pale yellow solid to precipitate instantly. More water (100 mL) was added and diethyl ether (100 mL) was added. The suspension was vacuum filtered. The solids were suction dried to afford the title compound as a pale yellow powder (2.73 g); microanalysis for $C_7H_6BNO_2S \cdot H_3PO_4$ % C (calc/found) 30.35/31.41, % H, 3.27/3.24, % N, 5.06/5.04, % S 11.58/11.93, % P 11.18/8.58; $^1$H-NMR (400 MHz, DMSO-$d_6$, CDCl$_3$, CD$_3$OD, D$_2$O mixture) δ 9.01 (d, 1H, J=1.0 Hz), 8.26 (d, 1H, J=6.0 Hz), 7.94 (s, 1H), 7.91-7.83 (m, 1H); MS (APCI$^+$) m/z 180 (MH$^+$).

Step ii: 1-(6-methylpyridin-2-yl)hydrazine. A mixture of 2-bromo-6-methyl-pyridine (602.10 g) and hydrazine hydrate (1570 ml) was refluxed at 120° C. for 6 hours, and then stirred at room temperature for about 48 hours. The solid separated was extracted with diethylether (3×1.5 L) and the combined ether extracts were washed with brine, dried over Na$_2$SO$_4$, filtered and concentrated (~430 g). The residue was stirred in a mixture of ether (200 ml) and hexane (1.5 L), filtered and washed with 5% diethylether in hexane to give a pale yellow solid (sticky). The solid was vacuum distilled at 106-113° C./2 mm, which solidified instantly. The solid was then dissolved in 2 L of diethylether and precipitated by adding 2 L of hexane, filtered and vacuum dried to give 1-(6-methylpyridin-2-yl)hydrazine as white solid (240 g).

Alternatively, 1-(6-methyl-pyridin-2-yl)-hydrazine was also synthesized as follows: A jacketed reaction flask was equipped with mechanical stirrer, nitrogen inlet, and reflux condenser and the jacket was cooled to 10° C. The reactor was programmed to automatically cool to 0° C. if at any point the internal temperature exceeded 80° C. The reactor was purged with a steady stream of nitrogen gas. To the reactor was charged 25 g (0.225 mol) of 2-fluoro-6-methylpyridine followed by 100 ml of isopropanol and the jacket temperature was adjusted to 73° C. (corresponding to an internal temperature of 70° C.). To the reactor was charged 44 g (0.90 mol) of 65% aqueous hydrazine and the mixture was stirred overnight with the jacket set at 70° C. The reactor contents were diluted with 125 ml of methyl t-butyl ether (MTBE) and 13 ml of saturated brine to give two layers which were separated. The aqueous layer was extracted with 2×60 ml of MTBE. The combined organic layers were combined and dried over sodium sulfate (anhydrous). The drying agent was removed by filtration and the organic filtrate was concentrated by rotary evaporation. The resulting oil solidified upon standing to give the desired product (21.1 g) as a white solid.

Step iii: 4-methyl-2-(6-methyl-pyridin-2-yl)-2H-pyrazol-3-ol. To a stirring mixture of sodium methoxide (13.6 g) in anhydrous tetrahydrofuran (50 mL) under a nitrogen atmosphere at room temperature in an oven-dried 500 mL three-neck reaction vessel was added anhydrous methyl formate (12.6 mL). The mixture frothed and to the suspension was added ethyl formate (28.7 mL) with a slow, steady stream via syringe while swirling the reaction vessel by hand to facilitate more efficient mixture of the suspension. The subsequent mixture was stirred at room temperature for five hours. Glacial acetic acid (14 mL) was added while the reaction vessel was swirled vigorously by hand for several minutes to facilitate more efficient mixture. The subsequent suspension was stirred overnight and was filtered through Celite. The Celite filter plug was washed twice with diethyl ether (2×200 mL) and suctioned. The filtrate produced a sparse white solid precipitate that was removed by a further vacuum filtration through a medium fritted Buchner funnel. The subsequent filtrate was concentrated under reduced pressure (water bath temperature=45° C.) to afford a clear, lightly colored oil (approximately 15 g). The oil possessed the distinct odor of acetic acid. The oil was dissolved in absolute ethanol (50 mL). To this solution was added solid (6-methyl-pyridin-2-yl)-hydrazine (5.4 g). The stirring mixture was brought to gentle reflux under a nitrogen atmosphere for four days. The mixture was concentrated under reduced pressure and the afforded orange oil was dissolved in dichloromethane (50 mL). The dichloromethane solution was applied to a 400-g Analogix flash silica cartridge on a Biotage instrument. Elution on the Biotage instrument with a gradient (100% heptane to 70% ethyl acetate in heptane over four column volumes, or 2400 mL). The fractions were dried down to afford a solid (7.1 g).

Alternatively, 4-Methyl-2-(6-methyl-pyridin-2-yl)-2H-pyrazol-3-ol was also produced as follows:

To a solution of ethyl formate (117.5 g) and ethyl propionate (54.0 g) in 40 ml of tetrahydrofuran (THF) was added, drop-wise, potassium t-butoxide (502 ml of a 1.0 molar solution in THF) at ambient temperature over approximately 0.5 hour. A white precipitate began to form along with some bubbling. After another 7.5 hours the reaction was filtered, the solid was washed with diethyl ether and then dried under vacuum at 40° C. for 16 hours to give potassium 2-ethoxycarbonyl-propen-1-olate as a grey powder (23.5 g).

To a solution of this potassium salt (17.6 g) in 450 ml of 1-propanol was added (6-Methyl-pyridin-2-yl)-hydrazine (11.7 g) followed by acetic acid (6.5 ml). After stirring for 10 minutes the mixture was heated at gentle reflux for 5 hours. More acetic acid (5.5 ml) was added and reflux was continued for a further 16 hours.

The solvent was removed under vacuum. The resulting residue was diluted with ethyl acetate (350 ml) and the solution was carefully washed with saturated sodium bicarbonate solution (200 ml) until the remaining acetic acid was neutralized. The phases were separated and the aqueous phase was extracted with ethyl acetate (50 ml). The organic phases were combined and then washed with water (100 ml), then brine (100 ml) and dried over magnesium sulfate. The drying agent was removed by filtration and the solvent was removed under vacuum to give the product as an orange solid (16.26 g).

Step iv: Trifluoro-methanesulfonic acid 4-methyl-2-(6-methyl-pyridin-2-yl)-2H-pyrazol-3-yl ester. To a stirring mixture of a dichloromethane solution of 4-methyl-2-(6-methyl-pyridin-2-yl)-2H-pyrazol-3-ol (13.39 g in 50 mL of dichloromethane) and triethylamine (11 mL) in additional dichloromethane (50 mL more, 100 mL total dichloromethane) at −78° C. under a nitrogen atmosphere was added triflic anhydride (13.3 mL) with a slow, steady stream via syringe over five minutes. The cold bath was removed and the mixture was allowed to warm gradually over one hour, thirty minutes to room temperature. The mixture was concentrated under reduced pressure and the concentrate was purified by flash silica chromatography. Elution with a gradient (100% heptane to 30% ethyl acetate in heptane over three column volumes, or 1800 mL, then 30% to 45% ethyl acetate over two additional column volumes, or 1200 mL) through a 400-g Analogix flash silica cartridge on the Biotage instrument afforded the title compound as a clear colorless oil (18.04 g). $^1$H-NMR (400 MHz, CDCl$_3$) δ 7.68 (m, 1H), 7.59 (d, J=8.0 Hz, 1H), 7.50 (s, 1H), 7.07 (d, J=7.4 Hz, 1H), 2.56 (s, 3H), 2.07 (s, 3H); $^{19}$F-NMR (376 MHz, CDCl$_3$) δ −74.12 (s, 3F); $^{13}$C-NMR (100 MHz, CDCl$_3$) δ 157.9, 151.1, 141.3, 139.5, 139.0, 122.0, 118.6 (quartet, $J_{C-F}$=321.0 Hz), 111.9, 108.7, 23.6, 7.3; MS (APCI$^+$) m/z 322.

Step v: 2-[4-Methyl-2-(6-methyl-pyridin-2-yl)-2H-pyrazol-3-yl]-thieno[3,2-c]pyridine. An oven-dried three-neck round-bottom flask equipped with reflux condenser and gas inlet valve was charged with thieno[3,2-c]pyridine-2-boronic acid trihydrogen phosphate (1.0 g), trifluoro-methanesulfonic acid 4-methyl-2-(6-methyl-pyridin-2-yl)-2H-pyrazol-3-yl ester (1.16 g), potassium phosphate tribasic (2.3 g), 1,4-dioxane (30 mL), dichloro[1,1'-bis(diphenylphosphino)ferrocene]palladium (II) dichloromethane adduct (0.60 g), and 1,1'-bis(diphenylphosphino)ferrocene (0.40 g) and the stirring mixture was brought to reflux under a nitrogen atmosphere for 18 hours. The reaction mixture was diluted with ethyl acetate (250 mL) and the solution was treated with activated carbon and filtered through Celite. The filtrate was concentrated under reduced pressure and the concentrate was purified by silica gel chromatography. Elution through a 120 g RediSep flash silica cartridge on a Biotage system with 100% heptane to 100% ethyl acetate over 1800 mL followed by 100% ethyl acetate until material with the desired mass elutes afforded an oil (1.2 g); MS (APCI$^+$) m/z 307 (MH$^+$). The product was further purified by dissolving in acetonitrile (30 mL) and dividing into two equal portions. After filtration, the solutions were sequentially purified by prep HPLC (Waters prep HPLC system; Stationary phase: Waters DeltPak C18 5 ☐M, 100 Angstrom, 300×50 mm I.D., P/N 011801, WAT 011801, No. 330009125W; Mobile phase 90:10 to 50:50 water-acetonitrile with 0.1% formic acid over 30 minutes). The combined fractions were concentrated under reduced pressure to an aqueous solution, removing the acetonitrile. The clear aqueous solution was treated with saturated aqueous potassium carbonate to give a cloudy white suspension. The suspension was allowed to stand at room temperature overnight. The solid white precipitate that had formed was collected by vacuum filtration and was dried in the vacuum oven (77° C.) overnight to afford the title compound as a white solid (0.506 g). melting point 157-158° c.

The $^1$H NMR and mass spec. analytical data for Examples 1-7 are reported below in Table 1:

TABLE 1

| Example | $^1$H NMR | MS |
|---|---|---|
| 1 | $^1$H NMR (400 MHz, d6-DMSO) δ 9.06 (d, J = 0.975 Hz, 1H), 8.38 (d, J = 5.5 Hz, 1H), 7.98 (m, 1H), 7.91 (t, J = 7.8 Hz, 1H), 7.84 (d, J = 1.8 Hz, 1H), 7.66 (s, 1H), 7.50 (d, J = 8.0 Hz, 1H), 7.35 (d, J = 8.2 Hz, | MS (APCI) m/z 293.1 (M + H)$^+$ |
| 2 | $^1$H NMR (400 MHz, DMSO-d$_6$) δ ppm 9.08 (s, 1H), 8.40 (d, J = 5.5 Hz, 1H), 8.01 (dd, J = 0.78, 5.7 Hz, 1H), 7.89 (t, J = 7.9 Hz, 1H), 7.64 (s, 1H), 7.50 (d, J = 8.0 Hz, 1H), 7.32 (d, J = 7.6 Hz, 1H), 6.76 (s, 1H), 2.34 (s, | MS (APCI, M + 1) 307.3 |
| 3 | $^1$H NMR (400 MHz, DMSO-d$_6$) δ ppm 9.07 (s, 1H), 8.40 (d, J = 5.7 Hz, 1H), 8.00 (dd, J = 0.78, 5.7 Hz, 1H), 7.89 (t, J = 7.8 Hz, 1H), 7.65 (s, 1H), 7.50 (d, J = 7.8 Hz, 1H), 7.32 (d, J = 7.6 Hz, 1H), 6.81 (s, 1H), 2.68 (q, | MS (APCI) m/z 321.2 (M + H)+ |

TABLE 1-continued

| Example | $^1$H NMR | MS |
|---|---|---|
| 4 | $^1$H NMR (400 MHz, DMSO-d$_6$) δ ppm 9.12 (s, 1H), 8.42 (dd, J = 5.6, 1.3 Hz, 1H), 8.03 (d, J = 5.5 Hz, 1H), 7.83 (m, 1H), 7.57 (s, 1H), 7.50 (d, J = 8.0 Hz, 1H), 7.19 (d, J = 7.6 Hz, 1H), 2.53 (q, under DMSO peak, | MS (APCI) m/z 321.2 (M + H)+ |
| 5 | $^1$H-NMR (400 MHz, CDCl$_3$) δ 8.99 (s, 1H), 8.41 (d, 1H, J = 5.5 Hz), 7.70-7.66 (m, 2H), 7.36 (d, 1H, J = 8.0 Hz), 7.27 (d, 1H, J = 0.5 Hz), 7.14 (d, 1H, J = 7.6 Hz), 2.89-2.83 (m, 4H), 2.56-2.49 (m, 2H), 2.47 (s, | MS (APCI$^+$) m/z 333 (MH$^+$). |
| 6 | $^1$H NMR (400 MHz, DMSO-d$_6$) δ ppm 9.11 (s, 1H), 8.41 (d, J = 5.5 Hz, 1H), 8.01 (d, J = 5.5 Hz. 1H), 7.79 (t, J = 7.7 Hz. 1H), 7.56 (s, 1H), 7.46 (d, J = 8.2 Hz, 1H), 7.14 (d, J = 7.4 Hz, 1H), 2.27 (s, 3H), 2.10 (s, 3H), 2.05 | MS (APCI) m/z 321.2 (M + H)+ |
| 7 | $^1$H-NMR (400 MHz, CDCl$_3$) δ ppm 9.06 (s, 1H), 8.44 (d, J = 5.7 Hz, 1H), 7.73 (d, J = 5.7 Hz, 1H), 7.65 (s, 1H), 7.62 (m, 1H), 7.37 (d, J = 8.0 Hz, 1H), 7.31 (s, 1H), 7.04 (d, J = 7.6 Hz, 1H), 2.27 (s, 3H), 2.18 (s, 3H) | (APCI$^+$) m/z 307 (M + H)$^+$ |

Example 8

2-[4-Methyl-2-(6-methyl-pyridin-2-yl)-2H-pyrazol-3-yl]-thieno[3,2-c]pyridine

Step i. 2-(4,4,5,5-tetramethyl-[1,3,2]dioxaborolan-2-yl)-thieno[3,2-c]pyridine. A solution of thieno[3,2-c]pyridine (5.0 g) in 100 mL THF under a N$_2$ atmosphere was cooled to −78° C. (acetone/dry ice). n-Butyllithium (28 ml, 1.6M in hexanes, freshly opened bottle) was added dropwise over twenty minutes, while maintaining the internal temperature at or below −64° C. The mixture was stirred for one hour at −78° C. and triisopropylborate (freshly opened bottle, 10.2 ml) was subsequently added. The cold bath was removed, allowing the mixture to warm to room temperature over 30 minutes. The mixture was stirred at room temperature for one hour. A mixture of pinacol (5.9 g) in diethyl ether (20 mL) was added to the reaction mixture. After twenty minutes, glacial acetic acid (2.2 mL) was added and a precipitate formed in the reaction mixture. The reaction mixture was filtered through Celite, rinsing with chloroform until the UV-active material was eluted (approximately 2500 mL). The filtrate was extracted twice with 5% aqueous sodium hydroxide solution (approximately 500 mL total). The aqueous basic phase stood at room temperature overnight. The aqueous layer was cooled in a CH$_3$CN/dry ice bath and was neutralized with 10% aqueous hydrochloric acid while maintaining the internal temperature at or below 5° C. The neutralized aqueous solution was extracted into chloroform ten times. The combined extracts were dried over anhydrous magnesium sulfate and were concentrated under reduced pressure to obtain a solid. This product was combined with the products of three other reactions performed on the same scale in a similar manner to afford a combined solid (23.52 g). The combined solid was dissolved in approximately 1 L of boiling ethanol. The solution was allowed to cool to room temperature. After about four hours at room temperature, the solution was stored at 4° C. overnight. A tan-colored material precipitated from solution. The liquid was decanted off through a filter. The solid was dried in a vacuum oven (50° C.) for one hour to afford the title compound (14.02 g) as a tan solid; $^1$H-NMR (400 MHz, CDCl$_3$ with one drop of D$_2$O to completely dissolve) δ 1.39 (12 H, s), 7.89 (1 H, d, J=5.3 Hz), 7.97 (1 H, s), 8.45 (1 H, d, J=4.5 Hz), 9.18 (1 H, s); MS (APCI$^+$) m/z 262.

Alternatively, 2-(4,4,5,5-Tetramethyl-[1,3,2]dioxaborolan-2-yl)-thieno[3,2-c]pyridine was also produced as follows:

To a −70° C. solution of thieno[3,2-c]pyridine (21.6 g) in 400 mL of dry tetrahydrofuran under nitrogen gas was added n-butyl lithium (99.9 ml of a 1.6 molar solution in hexanes) over about 15-20 minutes keeping the temperature below −65° C. The solution became cloudy and dark brown. After 45 minutes tri-isopropyl borate (33.06 g) was added and the mixture became homogeneous. The mixture was stirred at −70 to −75° C. for 2 hours. The mixture was allowed to warm to −30° C., then a solution of pinacol in 100 mL of diethyl ether was added over 4 minutes. The reaction mixture became an orange homogeneous solution. The temperature was allowed to warm to 5° C. and held at that temperature for 1 hour. The reaction mixture was neutralized (pH 7) very slowly with 40 mL of 4M hydrochloric acid in 1,4-dioxane, keeping the temperature below 10° C. A precipitate formed. The reaction mixture was stirred for 1 hour and then the solid was collected by filtration. The solid was dried under vacuum at 40° C. for 16 hours. The dry solid (36 g) was stirred with 400 mL of water for 1.5 hours. The slurry was filtered and the solid collected. The solid was dried under a flow of air for 60 hours to give the desired product (34.5 g). $^1$H NMR (400 MHz, Chloroform-d) δ ppm 1.21 (s, 12 H) 7.66-7.70 (m, 1 H) 7.80 (d, J=0.78 Hz, 1 H) 8.28 (d, J=5.65 Hz, 1 H) 8.98 (d, J=0.97 Hz, 1 H).

Step ii: 2-[4-Methyl-2-(6-methyl-pyridin-2-yl)-2H-pyrazol-3-yl]-thieno[3,2-c]pyridine. An oven-dried 500 mL three-neck round-bottom flask equipped with reflux condenser and gas inlet valve was charged with 2-(4,4,5,5-tetramethyl-[1,3,2]dioxaborolan-2-yl)-thieno[3,2-c]pyridine (11.56 g), trifluoro-methanesulfonic acid 5-ethyl-2-(6-methyl-pyridin-2-yl)-2H-pyrazol-3-yl ester (16.4 g), potassium phosphate tribasic (28 g), and 1,4-dioxane (300 mL). The reaction vessel was evacuated and flushed with nitrogen gas. The degassing and nitrogen flush was repeated twice. To the mixture were added dichloro[1,1'-bis(diphenylphosphino)ferrocene]palladium (II) dichloromethane adduct (7.3 g), and 1,1'-bis(diphenylphosphino)ferrocene (5.0 g) and the stirring mixture was degassed and flushed with nitrogen gas three more times, and subsequently brought gradually to gentle reflux over a thirty minute period. The mixture was stirred at reflux under nitrogen for 2.5 hours, and potassium fluoride (13 g) and water (1.2 mL) were subsequently added. The stirring mixture continued at reflux for fifteen minutes and was subsequently cooled slightly and filtered through Celite. The filter pad was washed with ethyl acetate (1 L) and the filtrate was treated with activated carbon. The carbon suspension was filtered through Celite. This filter pad was washed with additional ethyl acetate (300 mL), and the filtrate was concentrated under reduced pressure to afford a crude, red-brown oily residue (approximately 35 g). The residue was treated with several milliliters of absolute ethanol and was concentrated under reduced pressure. The residue was mixed with flash silica gel (100 g) and a solution of 5% methanol in ethyl acetate (200 mL). The mixture was filtered and the silica was washed twice with 200 mL of fresh 5% methanol in ethyl acetate solution. The filtrate was concentrated under reduced pressure to afford a red-brown oily residue (approximately 25 g). The residue was dissolved in several milliliters of ethanol. A precipitate subsequently formed upon standing, and was collected by vacuum filtration. The solids were washed with heptane to afford a sticky, red-orange powder (4.6 g). The ethanol-heptane filtrate yielded up a precipitate that was collected by vacuum filtration to give a beige solid (4.3 g). The beige solid was dissolved in absolute ethanol over steam. Gradual cooling of the clear solution produced a precipitate that was collected by vacuum filtration. Suction drying yielded a solid (2.25 g). The solid was boiled in and precipitated from absolute ethanol (15 mL) to give a white solid (1.62 g). The solid was boiled in and precipitated again from ethanol to provide the title compound as a white solid (1.20 g). $^1$H-NMR (400 MHz, CDCl$_3$) 9.12 (s, 1H), 8.46 (d, J=5.9 Hz, 1H), 7.94 (d, J=6.0 Hz, 1H), 7.68-7.64 (m, 2H), 7.48-7.43 (m, 2H), 7.04 (d, J=7.6 Hz, 1H), 2.21 (s, 3H), 2.19 (s, 3H); MS (APCI$^+$) m/z 307.

Example 9

2-[4-methyl-2-(6-methyl-pyridin-2-yl)-2H-pyrazol-3-yl]-thieno[3,2-c]pyridine

Step i: 2-methyl-6-(4-methyl-pyrazol-1-yl)-pyridine.
Reaction Condition 1

To a solution of 4-methyl-pyrazole (1.0 g) in 50 mL of anhydrous acetonitrile was added cesium carbonate (5.9 g), followed by 2-flouro-6-methylpyridine (1.5 g). The reaction mixture was stirred at reflux for 18 hours. The reaction mixture was filtered to remove cesium salts and then the filtrate was evaporated to give a crude oil. Purification by flash chromatography (silica gel, 20% ethyl acetate in heptane) provided, after drying, 1.32 g of the title compound as a yellow oil. $^1$H-NMR (400 MHz; DMSO-d$_6$) δ 8.34 (s, 1H), 7.80 (t, 1H), 7.63 (d, 1H), 7.59 (s, 1H), 7.13 (d, 1H), 2.47 (s, 3H), 2.08 (s, 3H); MS (APCI$^+$) m/z 174 (MH$^+$).
Reaction Condition 2

The reaction carried out for Step i for reaction 1 was carried out in a similar manner on a larger scale, starting with 4-methyl-pyrazole (5.0 g). 5.92 g of the title compound was produced.
Reaction Condition 3

Alternatively: starting with 4-methyl-pyrazole (1.0 g) in acetonitrile using 1.1 eq of potassium t-butoxide as base, 1.75 g of the title compound was produced.
Reaction Condition 4

Alternatively: starting with 4-methyl-pyrazole (1.0 g) in THF using 1.1 eq of potassium t-butoxide as base, 0.238 g of the title compound was produced.
Reaction Condition 5

In addition, the title compound of Step i was prepared as follows: To a suspension of 60% sodium hydride (8.04 g) in anhydrous DMF (40 mL) under a nitrogen atmosphere was added dropwise a solution of 4-methyl-pyrazol (15 g) in 30 ml of DMF in an ice bath over a 40 minute period. The resulting mixture was stirred at room temperature for 0.5 hour and then 2-flouro-6-methylpyridine (22.33 g) was added dropwise. The mixture was stirred at 80° C. for 3 hours and cooled down. The reaction mixture was poured in ice-water and extracted with ethyl acetate two times. The combined organic phase was washed with water and brine, dried over Na$_2$SO$_4$ and filtered. The filtrate was concentrated in vacuo to give a residue, which was purified by chromatography (2%-10% ethyl acetate in heptanes) to give 29.9 g of the title compound as a colorless oil.

Step ii: 2-(5-bromo-4-methylpyrazol-1-yl)-6-methylpyridine

To a cold (−60° C.) solution of 2-methyl-6-(4-methyl-pyrazol-1-yl)-pyridine (0.52 g) (prepared by Reaction Condition 1 in Step i) in 14 mL of anhydrous THF was added 1.33 mL of a 2.5M solution of n-butyllithium (0.21 g) in hexanes. The reaction mixture was stirred at −60° C. for one hour. A 10 mL solution of N-bromosuccinimide (0.59 g) in THF was added and then the final solution was stirred at −60° C. for 2 hours. Saturated ammonium chloride (20 mL) was added and then the reaction mixture was allowed to warm to 24° C. The reaction mixture was diluted with 300 mL of ethyl acetate and then the aqueous phase was separated. The organic phase was washed with additional saturated ammonium chloride (50 mL) and then with brine (50 mL). The organic layer was separated, dried (sodium sulfate), filtered, and then the filtrate was evaporated to give a crude red oil. Purification by flash chromatography (silica gel, 20% ethyl acetate in heptane) provided, after drying, 0.377 g of the title compound as a yellow oil; $^1$H-NMR (400 MHz; DMSO-$d_6$) δ 7.88 (t, 1H), 7.69 (s, 1H), 7.44 (s, 1H), 7.32 (s, 1H), 2.50 (s, 3H), 2.02 (s, 3H); MS (APCI$^+$) Mk 254 (MH$^+$).

Alternative Reaction Conditions: The compound of Step ii, 2-(5-bromo-4-methylpyrazol-1-yl)-6-methylpyridine, was also prepared as follows:

1.) Using similar reaction conditions as described above, 2-(5-bromo-4-methylpyrazol-1-yl)-6-methylpyridine, was prepared beginning with 2-Methyl-6-(4-methyl-pyrazol-1-yl)-pyridine (1.0 g) to provide the title compound (829 mg).
2.) Using similar reaction conditions as described above, 2-(5-bromo-4-methylpyrazol-1-yl)-6-methylpyridine, was prepared beginning with 2-Methyl-6-(4-methyl-pyrazol-1-yl)-pyridine (5.0 g) to provide the title compound (2.64 g).
3.) Using similar reaction conditions as described above, 2-(5-bromo-4-methylpyrazol-1-yl)-6-methylpyridine, was prepared beginning with 2-Methyl-6-(4-methyl-pyrazol-1-yl)-pyridine (1.0 g) to provide the title compound. In addition, 1,2-dibromotetrafluoroethane (1.5 equivalents) was used instead of N-bromosuccinimide (NBS) as the brominating agent (756 mg).

Step iii: 2-[4-methyl-2-(6-methyl-pyridin-2-yl)-2H-pyrazol-3-yl]-thieno[3,2-c]pyridine. To a solution of 2-(5-bromo-4-methylpyrazol-1-yl)-6-methylpyridine (2.0 g) in 20 mL of anhydrous 1,2-dimethoxyethane (DME) was added palladium bistriphenylphosphine dichloride (0.153 g). The reaction mixture was stirred at room temperature for 30 minutes and then 20 mL of water was added, followed by sodium bicarbonate (2.0 g) and then trifluoro-methanesulfonic acid 5-ethyl-2-(6-methyl-pyridin-2-yl)-2H-pyrazol-3-yl ester (3.1 g) was added. The reaction mixture was refluxed for 18 hours and then cooled to room temperature. The reaction mixture was diluted with 400 mL of diethyl ether and then the organic phase was washed with water (100 mL), saturated sodium bicarbonate (2×100 mL), and brine (100 mL). The organic layer was dried (magnesium sulfate), filtered, and then the filtrate was evaporated to give a yellow slurry. The mixture was diluted with 25 mL of ethyl acetate. The material did not all go into solution. The mixture was triturated for 15 minutes and then filtered (first filtration) to remove a yellow solid, which was rinsed with ethyl acetate (2×10 mL). The solid was air dried for 15 minutes to afford 448 mg of slightly impure product. The filtrate from the first filtration above was evaporated onto 6 g of silica gel and flash chromatographed (silica gel, 80% ethyl acetate in heptane, ethyl acetate, followed by 95% ethyl acetate in methanol) to give 0.565 g. The combined weight of the title compound was 1.01 g as a yellow solid. Precipitation from ethanol gave the title compound (0.764 g) as a yellow solid; melting point 155-156° C.; MS (APCI$^+$) m/z 307 (MH$^+$).

Example 10

2-[4-Methyl-2-(6-methyl-pyridin-2-yl)-2H-pyrazol-3-yl]-thieno[3,2-c]pyridine

Step i: 4-Bromo-pyridine. 4-Bromopyridine hydrochloride (20.0 g, 102.9 mmol) was partitioned between EtOAc and 5% NaHCO$_3$. The layers were separated, and the aqueous phase extracted with EtOAc. The combined organic extracts were washed with water and brine, dried over Na$_2$SO$_4$, and evaporated under reduced pressure in a 40° C. bath to provide 13.7 g (84%) of a volatile oil which was used immediately in the next step.

Step ii: 4-Bromo-pyridine-3-carbaldehyde. A suspension of 4-bromopyridine (13.7 g, 86.8 mmol) in 300 mL THF was purged with N$_2$ and cooled to −78° C. under an atmosphere of dry N$_2$. A solution of lithium diisopropylamide (2.0 M solution in heptane/THF/ethylbenzene, 43.4 mL, 86.8 mmol) was added over about 3 minutes. After 30 minutes, DMF (dimethylformamide) was added. The reaction mixture was maintained at −78° C. for 3 hours before allowing it to warm to ambient temperature overnight. The reaction mixture was quenched with saturated NH$_4$Cl and concentrated under reduced pressure to remove most of the THF. The aqueous mixture was extracted with EtOAc. The combined organic extracts were washed with water and brine, dried over Na$_2$SO$_4$, evaporated, and chromatographed (150 g Analogix silica gel column eluting with a gradient of 100% heptane to 30% EtOAc/heptane over 45 minutes). Fractions containing the product were combined and evaporated to give 2.20 g (13.6%) of the title compound. MS m/z 186 (M+H)$^+$.

Step iii: 1-Thieno[3,2-c]pyridin-2-yl-propan-1-one. To a solution of sodium hydrosulfide hydrate (1.31 g, 17.7 mmol) in 5 mL water was added DMF (30 mL) and K$_2$CO$_3$ (3.27 g, 23.7 mmol). The mixture was cooled to 0° C. in an ice bath before adding 1-bromo-2-butanone (2.68 g, 17.7 mmol). After 15 minutes, a solution of 4-bromopyridine-3-carbaldehyde (2.20 g, 11.8 mmol) in DMF (20 mL) was added. The reaction mixture was stirred at 45° C. for 2.5 days. The reaction mixture was diluted with water and extracted with EtOAc. The combined organic extracts were washed with water and brine, dried over Na$_2$SO$_4$, and evaporated to give the crude product (1.80 g, 80%) which was used in the next step without further purification. MS m/z 192 (M+H)$^+$.

Step iv: 3-Dimethylamino-2-methyl-1-thieno[3,2-c]pyridin-2-yl-propenone. A solution of 1-thieno[3,2-c]pyridin-2-yl-propan-1-one (1.80 g, 9.41 mmol) and dimethoxymethyl-dimethyl-amine (5.32 mL, 37.8 mmol) in DMF (20 mL) was purged with N$_2$ and heated to 80° C. for 18 hours. The reaction mixture was diluted with 1:1 water/brine and extracted with EtOAc. The organic extracts were washed with 1:1 water/brine and brine, dried over Na$_2$SO$_4$, and evaporated to give 2.1 g of crude material. The residue was repeatedly dissolved in toluene and evaporated until a constant residue weight was obtained. MS m/z 247 (M+H)$^+$.

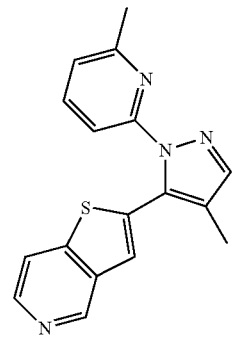 [SMILES: Cc1cccc(-n2ncc(C)c2-c2cc3cnccc3s2)n1]

Step v: 2-[4-Methyl-2-(6-methyl-pyridin-2-yl)-2H-pyrazol-3-yl]-thieno[3,2-c]pyridine. A solution of 3-dimethylamino-2-methyl-1-thieno[3,2-c]pyridin-2-yl-propenone (1.31 g, 5.32 mmol) in acetic acid (20 mL) was heated to 90° C. A solution of (6-methyl-pyridin-2-yl)-hydrazine in acetic acid (8 mL) was heated to 90° C. before adding to the 3-dimethylamino-2-methyl-1-thieno[3,2-c]pyridin-2-yl-propenone solution. The mixture was heated at 95° C. for 15 minutes before removing from heat and stirring at ambient temperature for 18 hours. The solvent was removed under reduced pressure, and the residue was evaporated from toluene twice. The residue thus obtained was chromatographed (Analogix 110 g silica gel column eluting with 100% $CH_3CN$) to provide 0.45 g (28%) of an orange oil.

A second method of preparing the compound of Step iii of Example 10, (1-thieno[3,2-c]pyridin-2-yl-propan-1-one) was also carried out as follows:

Step i. 4-Bromo-pyridine-3-carbaldehyde. A suspension of 4-bromopyridine hydrochloride (5.0 g, 25.7 mmol) in THF (100 mL) was purged with $N_2$ and cooled to −78° C. A solution of lithium diisopropylamide (2.0 M solution in heptane/THF/ethylbenzene, 27.0 mL, 54.0 mmol) was added over 3 minutes. After 30 minutes, DMF (8.56 mL, 110.6 mmol) was added. The reaction mixture was stirred at −78° C. for 15 minutes before rapidly warming to room temperature in a water bath. The reaction was allowed to stir at ambient temperature for 18 hours. The reaction was quenched with saturated $NH_4Cl$ (100 mL) and extracted with EtOAc. The combined organic extracts were washed with water and brine, dried over $Na_2SO_4$, evaporated, and chromatographed (Analogix 150 g silica gel column eluting with a gradient of 100% heptane 50% EtOAc/heptane over 1 hour) to give 1.50 g (31%) of the title compound as a light yellow solid. MS m/z 186 $(M+H)^+$.

Step ii: Thieno[3,2-c]pyridine-2-carboxylic acid methyl ester. To a solution of 4-bromo-pyridine-3-carbaldehyde (1.50 g, 8.06 mmol) in DMF (10 mL) and water (1 mL) was added $K_2CO_3$ (1.34 g, 9.68 mmol) and methyl thioglycolate (0.87 mL, 9.68 mmol). The mixture was heated at 45° C. for 18 hours. The reaction mixture was removed from the heating bath and diluted with water (50 mL). After 1 hour, the fluffy solid that formed was filtered and washed with water. The material thus obtained was dried in a 60° C. vacuum oven to a constant weight of 0.92 g (59%). MS m/z 194 $(M+H)^+$.

Step iii. Thieno[3,2-c]pyridine-2-carboxylic acid methoxy-methyl-amide. A suspension of O,N-dimethylhydroxylamine hydrochloride (2.32 g, 23.8 mmol) in THF (20 mL) was purged with $N_2$ and cooled to −78° C. before adding n-butyllithium (1.6 M in hexanes, 30.0 mL, 48.1 mmol). Removed bath and stirred 15 minutes before replacing the bath and adding a solution of thieno[3,2-c]pyridine-2-carboxylic acid methyl ester (0.92 g, 4.76 mmol) in THF (10 mL). After 45 minutes, saturated $NH_4Cl$ was added. The mixture was diluted with EtOAc; washed with water, 1 M HCl, water, 5% $NaHCO_3$, water, and brine; dried over $Na_2SO_4$, and evaporated to give 0.54 g (51%) of an oil which solidified upon standing. The product thus obtained was used in the next step without further purification. MS m/z 223 $(M+H)^+$.

Step iv. 1-Thieno[3,2-c]pyridin-2-yl-propan-1-one. Thieno[3,2-c]pyridine-2-carboxylic acid methoxy-methyl-amide (0.54 g, 2.43 mmol) was dissolved in THF (10 mL), purged with $N_2$, and cooled to 0° C. in an ice bath. Ethyl magnesium bromide (3 M in ether, 2.43 mL, 7.29 mmol) was added, and the reaction was allowed to warm to ambient temperature overnight. The reaction mixture was not purified further. MS m/z 192 $(M+H)^+$.

A third second method of preparing the compound of Step iii of Example 10, (1-thieno[3,2-c]pyridin-2-yl-propan-1-one) was also carried out as follows:

Step i: N-methoxy-N-methyl-propionamide. To a stirring mixture of O,N-dimethyl-hydroxylamine hydrochloride (11.1 g) and propionyl chloride (9.4 mL) in dichloromethane (300 mL) at 0° C. under a nitrogen atmosphere was added pyridine (18.2 mL). The cold bath was removed and the mixture was allowed to warm gradually to room temperature, at which temperature it stirred over the weekend. A white precipitate had formed in the stirring mixture. The mixture was treated with 10% aqueous hydrochloric acid and was stirred until the precipitate had dissolved in the biphasic solution. The layers were separated and the dichloromethane phase was washed with saturated aqueous sodium bicarbonate (100 mL) and brine solution (100 mL), was dried over anhydrous magnesium sulfate, and was concentrated under reduced pressure to afford the title compound as a clear colorless oil (12.05 g); $^1$H-NMR (400 MHz; $CDCl_3$) δ 3.62 (s, 3H), 3.11 (s, 3H), 2.38 (quartet, J=7.6 Hz, 2H), 1.07 (t, J=7.6 Hz, 3H); $^{13}$C-NMR (100 MHz; $CDCl_3$) δ 175.5, 61.3, 32.5, 25.4, 8.9; MS $(APCI^+)$ m/z 118 $(MH^+)$.

Step ii: 1-thieno[3,2-c]pyridin-2-yl-propan-1-one. To a stirring mixture of thieno[3,2-c]pyridine (1.0 g) in anhydrous tetrahydrofuran (50 mL) at −40° C. (acetonitrile-dry ice bath) was added a solution of n-butyllithium (1.6 M, 4.7 mL) in hexanes. The mixture was cooled to −78° C. followed by the subsequent addition of a solution of N-methoxy-N-methyl-propionamide (0.97 g) in anhydrous tetrahydrofuran (10 mL). The cold bath was removed and the reaction mixture was allowed to warm gradually to room temperature. The mixture was stirred overnight (14 hours). The mixture was treated with saturated aqueous ammonium chloride (150 mL). The mixture was then extracted with ethyl acetate (500 mL), and the extract was washed with brine solution (100 mL). The organic phase was dried over anhydrous potassium carbonate and was concentrated under reduced pressure, reconstituted in chloroform, and concentrated again under reduced pressure to afford the orange-brown semisolid (1.17 g). The semisolid was purified by flash silica chromatography using an Analogix silica column (115 g silica), eluting with 0-30% ethyl acetate/heptane, then 30-60% ethyl acetate/heptane. Concentration of fractions containing product gave 0.49 g of product. Starting material (0.45 g) was also isolated by evaporation of appropriate fractions.

Example 11

2-[4-Methyl-2-(6-methyl-pyridin-2-yl)-2H-pyrazol-3-yl]-thieno[3,2-c]pyridine

A 500 mL three-neck round-bottom flask equipped with reflux condenser and gas inlet valve was charged with 2-(4,4,5,5-tetramethyl-[1,3,2]dioxaborolan-2-yl)-thieno[3,2-c]pyridine (10 g), trifluoro-methanesulfonic acid 4-methyl-2-(6-methyl-pyridin-2-yl)-2H-pyrazol-3-yl ester (14 g), potassium phosphate tribasic (24 g), and 1,4-dioxane (200 mL). The reaction vessel was evacuated and flushed with nitrogen gas. The degassing and nitrogen flush was repeated twice. To the mixture were added dichloro[1,1′-bis(diphenylphosphino)ferrocene]palladium (II) dichloromethane adduct (3.2 g), 1,1′-bis(diphenylphosphino)ferrocene (2.2 g), potassium fluoride (11 g), and water (1 mL) and the stirring mixture was degassed and flushed with nitrogen gas three more times, and subsequently brought gradually to 80° C. over a twenty minute period. The mixture was stirred at 80° C. for ten minutes and was subsequently cooled gradually to room temperature as it stood overnight. The mixture was vacuum filtered through Celite and was washed through the filter plug with two portions of ethyl acetate (800 mL and 600 mL). The filtrates were combined and concentrated under reduced pressure to give a dark residue. The residue was dissolved in dichloromethane (200 mL). A solid precipitated and was removed by vacuum filtration. The filtrate was concentrated under reduced pressure to afford an orange-brown solid (20 g). The solid was treated with room-temperature acetonitrile (200 mL) and the resulting suspension was swirled and vacuum filtered to afford a yellow solid (9.1 g). This second solid was dissolved in boiling acetonitrile over a steam bath (75 mL solution volume hot) and the orange solution was allowed to cool to room temperature over thirty minutes. A solid precipitated, and the flask was sealed with and stored at 4° C. overnight. The precipitate was vacuum filtered and suction dried to afford the title compound as an off-white solid (4.80 g). This solid was combined with batches of solid isolated in a similar manner from other experiments (21.5 g total mass) to give a combined solid.

The combined solid was further combined with the solid (8.92 g) obtained from the following experiment:

Solutions of 3-dimethylamino-2-methyl-1-thieno[3,2-c]pyridin-2-yl-propenone (31.35 g) in glacial acetic acid (500 mL) and (6-methyl-pyridin-2-yl)-hydrazine (15.67 g) in glacial acetic acid (200 mL) were purged with dry nitrogen and heated to 90° C. under nitrogen gas. The two mixtures were combined and heated to 95° C. for 15 minutes. Heating was discontinued and the reaction mixture was allowed to cool and stir at room temperature overnight. The crude reaction mixture was concentrated to about 100 g of a dark oil under reduced pressure. The residue was dissolved in toluene and evaporated to about 70 g. A strong smell of acetic acid was evident, so the evaporate was dissolved in toluene and evaporated to about 70 g of an oil. Although the residue thus obtained still had a faint acetic acid odor, it was dissolved in acetonitrile (200 mL) and allowed to stand at room temperature. After 2.5 days, no precipitate had formed, so the solution was evaporated under reduced pressure in a 60° C. bath. The resulting oil was dissolved in acetonitrile (about 200 mL) and allowed to cool to room temperature. A small amount of precipitate had formed which was collected and washed with a small amount of acetonitrile. Upon filtration, a large amount of solid precipitated from the mother liquor. The precipitate was collected and washed with a small amount of acetonitrile. Upon drying in a 60° C. vacuum oven, 12.05 g of material was obtained. The solid thus obtained was reisolated from 250 mL boiling acetonitrile to provide, after drying to constant weight in a vacuum oven at 60° C., the solid (8.92 g) 2-[4-methyl-2-(6-methyl-pyridin-2-yl)-2H-pyrazol-3-yl]-thieno[3,2-c]pyridine.

The combined 21.5 g and 8.92 g batches were suspended in acetonitrile to 500 mL total volume. The suspension was heated over a steam bath to boiling. Most of the solid dissolved into solution, but some particulates remained undissolved and were removed by hot vacuum filtration. The filtrate collected in the 2 L filter flask rapidly yielded a white solid precipitate. Acetonitrile was added to 600 mL volume. The filtrate was boiled over a steam bath until all solids dissolved. The flask was removed from the steam bath and the mixture was cooled gradually to room temperature as it stood on the bench for 2.5 hours. A white solid formed from solution over that time and was collected by vacuum filtration to afford the title compound as a white solid (24.85 g); $^1$H-NMR (400 MHz, CDCl$_3$) δ 9.06 (d, J=0.8 Hz, 1H), 8.43 (d, J=5.7 Hz, 1H), 7.72 (ddd, J=5.7, 1.0, 0.8 Hz, 1H), 7.64 (s, 1H), 7.61 (t, J=7.8 Hz, 1H), 7.36 (d, J=8.0 Hz, 1H), 7.31 (d, J=0.8 Hz, 1H), 7.03 (d, J=7.6 Hz, 1H), 2.26 (s, 3H), 2.18 (s, 3H); MS (APCI$^+$) m/z 307 (MH$^+$), (APCI) m/z 305 (M−H$^+$).

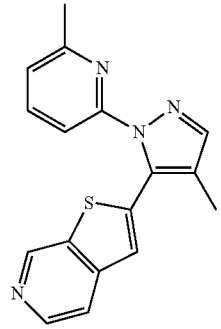 [SMILES: Cc1cccc(-n2ncc(C)c2-c2cc3ccncc3s2)n1]

Example 12

2-(4-methyl-1-(6-methylpyridin-2-yl)-1H-pyrazol-5-yl)thieno[2,3-c]pyridine

Thieno[2,3-c]pyridine of Step iii, Example 12 has been synthesized previously (see e.g., Graulich at al. (2004) Synthesis 12: 1935-1937; Graulich et al. (2005) J. Med. Chem. 48(15): 4972-4982).

Step i. (2,2-Dimethoxy-ethyl)-thiophen-2-ylmethylene-amine. A solution of thiophene-2-carboxaldehyde (7.5 mL, 82.3 mmol, Alfa Aesar), aminoacetaldehyde dimethyl acetal (8.82 mL, 82.3 mmol, Alfa Aesar) in 100 mL toluene was heated to 115° C. using a Dean-Stark trap to remove water. After 3 hours, the reaction was cooled to room temperature. The reaction was placed on a rotary evaporator to evaporate the toluene, which yielded a brown liquid (about 17.3 g), which was used without further manipulation in the next step. $^1$H NMR (400 MHz, CHLOROFORM-d) δ ppm 3.42 (6H, s), 3.73 (1H, d, J=5.3 Hz), 4.65 (1H, t, J=5.3 Hz), 7.07-7.41 (3H, m).

Step ii. {[(2,2-Dimethoxy-ethyl)-ethoxycarbonyl-amino]-thiophen-2-yl-methyl}-phosphonic acid dimethyl ester. To the oil obtained in Step i (16.3 g, 82.3 mmol) was added 60 mL THF under a N$_2$ atmosphere. The reaction was cooled to −10° C. (MeOH/ice) and fitted with an internal thermometer. Ethyl chloroformate (7.9 mL, 82.3 mmol) was added dropwise keeping the internal temperature at or below −9.5° C. The reaction was stirred for 10 minutes at −10° C. and then the bath was removed and the reaction was allowed to warm to room temperature. Using an ice bath as a heat sink, trimethyl phosphite (10.7 mL, 90.5 mmol) was added. The reaction was allowed to gradually warm to room temperature and was stirred overnight. The solvent was removed on a rotary evaporator. Toluene was added and evaporated on a rotary evaporator. The toluene addition and evaporation was then carried out a second time.

The resulting thick brown oil was purified by column chromatography (Biotage Horizon system, 330 g Isco RediSep column, 0-100% EtOAc/hexane over 1 column volume then hold at 100% EtOAc). The desired fractions were combined and concentrated to give 23.48 g of a thick, brown oil.

Step iii. Thieno[2,3-c]pyridine. The material from Step ii (23.5 g, 61.6 mmol), was dissolved in 100 mL $CH_2Cl_2$. The three neck flask was fitted with a reflux condenser and internal thermometer under $N_2$ atmosphere. The flask was evacuated and purged with nitrogen. Titanium (IV) chloride (40 mL, 369 mmol) was added to the reaction slowly. The reaction temperature was maintained at around 40° C. After about 15 mL were added, the reaction was placed in an ice bath to control the temperature. The reaction was allowed to gradually warm to room temperature before heating to 40° C. overnight. The reaction was heated to 40° C. for 18 hours, then cooled to room temperature. The reaction contents were poured, in portions, into a large beaker containing 200 g of ice and 200 mL $NH_4OH$ with lots of fuming observed. The reaction was stirred vigorously for a few minutes. The reaction was filtered and the solid was rinsed with $CHCl_3$ (3×100 mL).

The biphasic filtrate was transferred to a separatory funnel and the layers were separated. The organic layer was extracted into 1 N HCl (2×100 mL). The aqueous HCl layer was washed with 20 mL $CH_2Cl_2$ and carefully basified with concentrated $NH_4OH$ until a pH of about 9 was reached. The product was extracted into $CH_2Cl_2$ (3×100). The organic layer was dried over $MgSO_4$, filtered, concentrated to an orange oil that solidified to an orange solid. The crude material was purified by column chromatography (Biotage Horizon system, 120 g Isco RediSep column, equilibrate with 100% heptane, elute with 45% EtOAc/heptane). A white solid was isolated (4.20 g). $^1$H NMR (400 MHz, DMSO-$d_6$) δ ppm 7.56 (1 H, dd, J=5.5, 0.8 Hz), 7.86 (1 H, dd, J=5.5, 1.0 Hz), 8.10 (1 H, d, J=5.3 Hz), 8.46 (1 H, d, J=5.5 Hz), 9.25 (1 H, s). $^1$H NMR (400 MHz, CHLOROFORM-d) δ ppm 7.40 (1 H, d, J=5.5 Hz), 7.74 (2 H, m), 8.52 (1 H, d, J=5.5 Hz), 9.19 (1 H, s). MS (APCI, M+1) 136.0.

Step iv. Thieno[2,3-c]pyridin-2-ylboronic acid trihydrogen phosphate. A three neck flask fitted with an internal thermometer containing the material from Step iii (4.12 g, 30.5 mmol) was evacuated and then filled with nitrogen atmosphere. THF (50 mL) was added and the solution cooled to −44° C. ($CH_3CN$/dry ice). n-Butyllithium (1.6M/ hexane, 21 mL, 34 mmol) was added over 10 minutes, while maintaining the internal temperature at or below −35° C. The reaction was stirred at −33 to −45° C. for 75 minutes. Triisopropyl borate (8.4 mL, 36.6 mmol) was added and the cooling bath removed. The reaction was stirred for one hour then phosphoric acid (85% aqueous, 2.5 mL, 33.5 mmol) was added. The reaction was diluted with 10 mL water resulting in a precipitate. The reaction was stirred vigorously for 15 minutes. A yellow solid was collected by filtration, rinsing with EtOAc (about 50 mL) to provide a white powdery solid (9.57 g). Approximately half of the material was washed with 50 mL water to isolate 3.16 g of a pale pink solid. Both crops of material are the same as determined by spectral data. $^1$H NMR (400 MHz, METHANOL-$d_4$) δ ppm 7.87 (1 H, d, J=5.5 Hz), 7.95 (1 H, s), 8.41 (1 H, d, J=5.7 Hz), 9.11 (1 H, s).

Step v. 2-(4-methyl-1-(6-methylpyridin-2-yl)-1H-pyrazol-5-yl)thieno[2,3-c]pyridine. In a 250 mL three neck flask was added trifluoro-methanesulfonic acid 4- methyl-2-(6-methyl-pyridin-2-yl)-2H-pyrazol-3-yl ester (1.23 g, which may be synthesized as describe in Example 7, Step iv), the material from Step iv (2.00 g), potassium fluoride (1.11 g), potassium phosphate tribasic (2.44 g) in 50 mL dioxane. The flask was evacuated with a vacuum and purged with nitrogen gas. To this was added $PdCl_2$(dppf) (Strem, Dichloro[1,1'-bis(diphenylphosphino)ferrocene]palladium (II) dichloromethane adduct, 280 mg)) and dppf ligand (Strem, 1,1'-bis(diphenylphosphino)ferrocene, 212 mg) and water (0.10 mL). The reaction was heated to 80-111° C. for 2.5 hours then cooled to room temperature. The reaction was combined with material from another reaction which was run in a similar manner. The crude reaction material was filtered through a pad of Celite rinsing with EtOAc (about 750 mL). The filtrate was concentrated to dryness on rotary evaporator. The dark residue was diluted with $CH_2Cl_2$ and the solid was filtered off. The $CH_2Cl_2$ filtrate was concentrated on a rotary evaporator to a black residue. The crude material was purified by filtering through a silica gel plug eluting with 50% EtOAc/hexane (about 800 mL total). The fractions from the silica gel plug filtration yielded two lots of material (one pure, one impure) These were concentrated to dryness separately. The impure material was triturated with $Et_2O$ and a white solid was collected by filtration. The filtrate was concentrated and the $Et_2O$ trituration was repeated to give 83 mg. The fractions containing only desired product plus the 83 mg batch were combined and purified together with the pure lot. About 5-10 mL of EtOH were added to the material, which was heated to boiling. Once all of the material was dissolved, it was removed from the heat and allowed to stand. A beige solid then began to precipitate. The mother liquors were decanted off and the precipitate was rinsed with a small amount of cold EtOH. The precipitate was dried in a 50° C. vacuum oven overnight to provide 550 mg of a beige solid. $^1$H NMR (400 MHz, $CDCl_3$) δ ppm 9.09 (1 H, s), 8.50 (1 H, d, J=5.7 Hz), 7.62-7.69 (3 H, m), 7.39 (1 H, d, 7.99 Hz), 7.27 (1 H, d, J=0.6 Hz), 7.04 (1 H, d, J=7.4 Hz), 2.25 (3 H, s), 2.19 (3 H, s). MS (APCI, M+1) 307.1. mp 124-125° C.

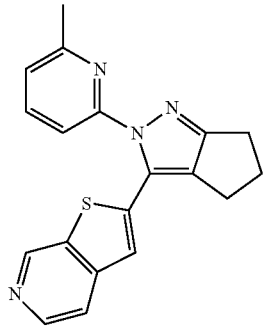 [SMILES: Cc1cccc(-n2nc3c(c2-c2cc4ccncc4s2)CCC3)n1]

Example 13

2-(2-(6-methylpyridin-2-yl)-2,4,5,6-tetrahydrocyclopenta[c]pyrazol-3-yl)thieno[2,3-c]pyridine In a 250 mL three neck flask was added trifluoro-methanesulfonic acid 2-(6-methyl-pyridin-2-yl)-2,4,5,6-tetrahydro-cyclopentapyrazol-3-yl ester (1.33 g, which may be synthesized as described in Example 5, Step iv), the material from Example 12, Step iv (2.00 g), potassium fluoride (1.11 g), potassium phosphate tribasic (2.44 g) in 45 mL dioxane. The flask was evacuated under reduced pressure and purged with nitrogen gas. To this was added $PdCl_2$(dppf) (Strem, Dichloro[1,1-bis(diphenylphosphino)ferrocene]palladium (II) dichloromethane adduct, 280 mg)) and dppf ligand (Strem, 1,1'-bis(diphenylphosphino)ferrocene, 212 mg) and water (0.10 mL). The reaction was heated to 80-111° C. for 3.5 hours and then cooled to room temperature. The reaction material was filtered through a pad of Celite rinsing with EtOAc (about 250 mL). The EtOAc filtrate was concentrated to dryness on a rotary evaporator. The resulting dark residue was diluted with $CH_2Cl_2$ and the solid was filtered off. The $CH_2Cl_2$ filtrate was concentrated on a rotary evaporator to a black residue that was diluted with $CH_3CN$ and sonicated. A tan solid (0.520 g) was collected by filtration. The filtrate was concentrated to dryness and purified by column chromatography (Biotage Horizon system, 12 g Analogix column, 0-50% EtOAc/heptane, then hold at 50% EtOAc/heptane) to yield about 300 mg of a solid. The 300 mg of the solid and the tan solid (0.520 g) were combined and diluted with about 10 mL EtOH, heated to boiling, filtered, and allowed to cool to room temperature. Solid material began to precipitate. After standing overnight at room temperature the mother liquors were decanted off and the remaining material was rinsed with a small amount of cold EtOH. The solid was dried in a 45° C. vacuum oven for 1.5 hours to provide 410 mg of a solid. $^1H$ NMR (400 MHz, $CDCl_3$) δ ppm 9.05 (1 H, s), 8.45 (1 H, d, J=5.7 Hz), 7.70 (1 H, t, J=7.7 Hz), 7.62 (1 H, d, J=5.7 Hz), 7.38 (1 H, d, J=7.9 Hz), 7.25 (1 H, d, J=1.2 Hz), 7.15 (1 H, d, J 7.6 Hz), 2.85-2.91 (4 H, m), 2.51-2.58 (2 H, m), 2.46 (3 H, s). MS (APCI, M+1) 333.1. mp 145-146° C.

Example 14

2-[4-methyl-2-(6-methylpyridin-2-yl)2H-pyrazolo-3-yl]thieno[3,2-c]pyridine

Trifluoro-methanesulfonic acid 4-methyl-2-(6-methyl-pyridin-2-yl)-2H-pyrazol-3-yl ester (36.6 g, 114 mmoL), potassium carbonate (39.4 g, 285 mmol), and 2-(4,4,5,5-Tetramethyl-[1,3,2]dioxaborolan-2-yl)-thieno[3,2-c]pyridine (31.2 g, 120 mmol) were slurried in toluene (300 mL), isopropyl alcohol (IPA) (75 mL) and water (75 mL). The reaction mixture was sequentially subjected to vacuum followed by purging with nitrogen. This was repeated for a total of five times.

Bis(triphenylphosphine)palladium(II) Chloride (4.4 g, 6.27 mmol) was added, and the reaction was heated to 78° C. After 2 hours the reaction mixture was allowed to cool. The aqueous layer was separated, and the organic layer was filtered to remove black catalyst residue. The organic layer was washed with water (80 mL). The organic layer was extracted with 3 M HCl (100 mL) and water (100 mL). Carbon (0.5 g) and celite (9 g) were added to the aqueous and the solution was concentrated to remove the residual toluene. The aqueous layer was filtered. The aqueous was made basic (pH=10) with the addition of 50% NaOH. A yellow solid precipitated. The solid was filtered, washed with water and dried by pulling air through it to give 24.1 g (69.1%) of a yellow solid. The solid was slurried in toluene (250 mL). The slurry was heated to 65° C. and filtered. The filtrate was concentrated. The residue was slurried in toluene (100 mL) and filtered. The cake was washed with toluene (40 mL). The cake was dried by pulling air through it to give 19.2 g (55%) of crude product.

The 19.2 g was combined with other similarly prepared samples to give 141.7 g. The combined solids were slurried in IPA (500 mL) and the slurry was heated to 83° C., but the solid did not all go into solution. IPA (300 mL) was added and the slurry heated to 83° C. to give a dark solution. The solution was allowed to cool to room temperature at 8° C./hour. The slurry was filtered, and the cake was washed with IPA (200 ml). The cake was dried at 50° C. for 60 hours to give 131.8 g of the desired product.

Biological Example 1

ALK-5 kinase assay methods have been described in the art (see e.g., Laping et al. (2002) Mol. Pharmacol. 2002; 62: 58-62). The compounds named in the specified Examples were tested as follows for inhibition of ALK-5 autophosphorylation activity and of the ALK-5 phosphorylation of α-Casein.

Materials:
  Buffer. 50 mM HEPES, pH 7.6, with 10 mM NaCl, 10 mM $MgCl_2$, and 1 mM DTT.
  GST-ALK-5 protein—0.44 mg/ml (roughly 7 µM stock). A 1:350 dilution gives a 20 nM stock, which translates to 2 nM final in assay. Human ALK-5 was expressed in Sf9 insect cells infected with Baculovirus expressing a ALK-5 truncation sequence (amino acids $H^{149}$-$M^{503}$), fused at the N-terminus to Glutathione S-transferase GST, in a pFastBac vector (Invitrogen). The cells were disrupted by sonication at 4° C. The lysate was centrifuged at 40,000×g for 45 minutes, and the supernatant applied to a 10 ml column of Glutathione Sepharose 4 Fast Flow (Amersham Biosciences) equilibrated with 100 mM Tris-HCl pH 7.6 buffer containing 300 mM NaCl, 10% glycerol, 1% NP40, 2 mM dithiothreitol (DTT) and one Protease Inhibitor complete EDTA-free tablet per 50 ml (Roche). The column was washed with 5 column volumes of 50 mM Tris HCl pH 8.0 containing 150 mN NaCl, 10% glycerol, 2 mM DTT and one Protease Inhibitor complete EDTA-free tablet per 100 ml. The column was eluted with wash buffer containing 8 mM reduced glutathione. Fractions were collected and dialyzed overnight in 20 mM Tris HCl pH 8.0 containing 10% glycerol, 150 mM NaCl, 2 mM DTT and 1 mM 4-(2-aminoethyl)-bezenesulfonyl fluoride.HCl (AEBSF) (Sigma) at 4° C.
  α-Casein (Sigma, #C8032) is made up at 2 mM in Buffer (50 mg/ml).
  Cold ATP contains 10 µM cold ATP (from a 10 mM stock in Buffer).
  Hot ATP consists of 0.5 µCi/well □-$^{33}$P-ATP (Amersham, AH9968) in Buffer.
  Assay Buffer—Per 10 ml Buffer
    1 ml of 500 mM HEPES (pH 7.6)
    20 µl of 5 M NaCl
    100 µl of 1 M $MgCl_2$
    10 µl of 1 M DTT (dithiothreitol)

Assay Method:
  In a 96 well filter-bottom plate (Millipore, #MSDV N6B 50), 58 µl Assay Buffer is added to reach well. Add 10 µl of Cold ATP mix in Assay Buffer, then 10 µl of a 1:10 dilution of α-Casein stock. Then add 2 µl of compound being tested (DMSO) at a 50× final concentration. Hot ATP mix (10 µl) is added, and the reaction is started with the addition of 10 µl of a 1:350 dilution of the ALK-5 protein (2 nM final) in Assay Buffer with 0.05% BSA (Bovine Serum Albumin). The reaction is mixed for 5 minutes at room temperature, and then continued for 145 minutes at room temperature. The reaction is then stopped with the addition of 100 µl of ice-cold 20% TCA (trichloroacetic acid). The assay is then incubated for at least 1 hour at 4° C., and then the contents of each well are filtered by suction through the filter. The wells are washed three times with 200 µl ice-cold 10% TCA. The plate bottom is blotted before and after removing plastic sub-base, and dried overnight at room temperature. Add 30

μl of scintillation fluid, and count 1 minute per well on a Wallac Tri-Lux scintillation counter.

The $IC_{50}$ (nM) values are reported in Table 2 below as the mean of two or more $IC_{50}$ values that were determined in one or more experiments. The number of determinations ("n") is reported within the parentheses. The individual values that produced the mean $IC_{50}$ values are listed inside the parentheses if there were 4 or fewer determinations. The Standard Error (SE) is reported as well. The Standard Error is the standard deviation divided by the number of determinations ("n").

TABLE 2

| Example | $IC_{50}$ (nM) |
|---------|----------------|
| 1 | 23.4 (n = 18); SE = 3.5 |
| 2 | 94.1 (n = 2; 111, 76.8); SE = 17.3 |
| 3 | 108 (n = 2; 121, 94.8); SE = 13.3 |
| 4 | 4.33 (n = 4; 1.0, 2.84, 7.82; SE = 1.51 |
| 5 | 12.9 (n = 4; 31, 12.5, 1.0, 7.24); SE = 6.46 |
| 6 | 35.2 (n = 2; 38.6, 31.8); SE = 3.41 |
| 7 | 6.65 (n = 16); SE = 0.61 |
| 12 | 7.94 (n = 2; 10.4, 5.47); SE = 2.48 |
| 13 | 18.9 (n = 2; 26.7, 11.2); SE = 7.73 |

Biological Example 2

ALK-5 gene reporter assay methods have been described in the art (see e.g., Maliekal et al. (2004) J Biol Chem 279(35):36287-36292). The compounds named in the specified Examples were tested as follows for inhibition of Smad binding element (SBE) luciferase reporter activity in TGFβ1 stimulated NIH-3T3 cells. The following luciferase assay employs NIH/3T3 (murine fibroblast) cells, which are transiently transfected with a Smad binding element (SBE) luciferase reporter construct. This expressed construct is responsive to agents that stimulate the Smad signaling pathway.

Materials:
  NIH-3T3 cells (ATCC CRL-1658)
  Dulbecco's Modified Eagle Medium with phenol red (Life Technologies 11965-092)
  Dulbecco's Modified Eagle Medium without phenol red (Life Technologies 21063-029)
  Fetal Bovine Serum (Life Technologies SH30071.03)
  Fugene (Roche 1814443)
  Opti-MEM I (Life Technologies 31985-070)
  Dual-Glo Luciferase Assay System (Promega E2940, E2980)
  Gentamycin solution (10 milligrams/millimeter)(Life Technologies 15710-064)
  96-Well Assay Plates, white, TCT (Corning Costar 3917)
  75 centimeter Tissue Culture Flasks (Corning Costar 430641)
  pRL-CMV vector (Promega Corporation, Madison, Wis., Product E2261) (pRL is a vector encoding a *Renilla reniformis* luciferase under the control of a constitutively active cytomegalovirus (CMV) promoter)
  Transforming Growth Factor $\square_1$-(R&D systems, Minneapolis, Minn., Product 240-B)
  pSBE4-LuGBV4 vector (also known as pSBE4-luc vector)(which contains 4 copies of a Smad Binding Element and firefly luciferase coding region) (Zawel et al. (1998) Mol Cell. 1(4):611-617).

Methods:
The NIH-3T3 cells are maintained in Dulbecco's Modified Eagle Medium with 10% Fetal Bovine Serum and 10 micrograms/ml Gentamycin. Cells are split every Monday, 1:5 to 1:10, and are split again on Wednesday. Cells are split on Friday, 1:20, for cells required for assay and maintenance on Monday. Do not let cells grow to total confluency.

Day 1, 0 Hours (Start of Experiment)
  Plate 1.6 million NIH/3T3 cells in a 75 centimeter flask for transfections using 15 milimeters of growth media (Dulbecco's Modified Eagle Medium, 10% Fetal Bovine Serum, 10 micrograms/millimeter Gentamycin).

Day 1, 7 Hours Post-Start of Experiment
  Prepare the transfection:
    a. In a 1.5 millimeter microcentrifuge tube, add 48 microliters of Fugene directly to 400 microliters of Opti-MEM. Incubate at room temperature for 5 minutes.
    b. During the above incubation period, aliquot 8 micrograms of SBE-luc and 0.16 micrograms of CMV-pRL to 400 microliters Opti-MEM.
    c. Add Fugene/Opti-MEM from step "a" to DNAs in step "b". Incubate at room temperature for 15 to 45 minutes.
    d. Add complexed DNAs to cells plated above (Day 1, 0 hours). It is not necessary to change media. Incubate overnight at 37° C., 5% $CO_2$.

Day 2, 24 Hours Post-Start of Experiment
  Prepare cell suspension(s) from transfected cells (Day 1, step 2) at a density of 200,000 cells/ml in Dulbecco's Modified Eagle Medium, 10% Fetal Bovine Serum, 10 micrograms/millimeter Gentamycin. Plate cells in assay plates (white TCT), 100 microliters/well for 96-well plates. This will put the number of cells at 20,000 cells/well. Incubate for 5-6 hours at 37° C., 5% $CO_2$.

Day 2, 31 Hours Post-Start of Experiment
  a. Prepare dose response plates if needed.
  b. Wash plate with 100 microliters Dulbecco's Modified Eagle Medium, 10 micrograms/millimeter Gentamycin without serum.
  c. Add 170 microliters/well of Dulbecco's Modified Eagle Medium, 10 micrograms/millimeter Gentamycin, 0.5% Fetal Bovine Serum,
  d. Transfer test compounds and controls to assay plates (white, TCT), 20 microliters of 10× stock for 96-well plates.
  e. After 30-60 minutes of treatment with compound, add 250 picograms/millimeter of Transforming Growth Factor $D_1$ to each well. (Add 10 microliters of a 20× stock).

Day 3, 51 Hours Post-Start of Experiment
  Assay Plates for Luciferase Activity.
    a. Reconstitute lyophilized Dual-Glo Luciferase Substrate with Dual-Glo Luciferase Buffer according to manufacturer's directions.
    b. Remove assay plates from the incubator and allow them to reach room temperature for 10 minutes.
    c. Aspirate media from the assay plate. Add 80 microliters diluted Steady-Glo Luciferase Substrate containing 1 parts Dulbecco's Modified Eagle Medium media without phenol red. Seal plates and incubate for at least 10 minutes at room temperature.
    d. Read on the Packard TopCount HTS plate reader using single photon counting (SPC) mode for 6 seconds/well to read the firely luciferase activity from pSBE4-Luc/BV4 pSBE4-luc.
    e. After reading plates for firefly luciferase activity, remove seals and add 40 microliters of Stop and Glo reagent to each well. Reseal plates and incubate for at least 10 minutes at room temperature. Read plates on Packard TopCount as with firefly luciferase, to read the *Renilla luciferase* activity from pRL.

The *Renilla luciferase* activity serves a transfection control. The firefly luciferase activity serves as the assay readout.

The luciferase assay activity is normalized to the *Renilla assay* activity for each particular sample.

The $IC_{50}$ (nM) values are reported in Table 3 below as the mean of two or more $IC_{50}$ values that were determined in one or more experiments. The number of determinations ("n") is reported within the parentheses. The individual values that produced the mean $IC_{50}$ values are listed inside the parentheses where n is 4 or less. The Standard Error (SE) is reported as well. The Standard Error is the standard deviation divided by the number of determinations ("n").

TABLE 3

| Example | $IC_{50}$ (nM) |
|---------|----------------|
| 1 | 149 (n = 4; 117, 133, 164, 183); SE = 14.9 |
| 2 | 440 (n = 3; 211, 504, 605); SE = 118 |
| 3 | 403 (n = 3; 286, 453, 471); SE = 58.9 |
| 4 | 21.5 (n = 3; 11.5, 26, 27); SE = 5.0 |
| 5 | 30.8 (n = 4; 22, 27, 30, 44); SE = 4.71 |
| 6 | 244 (n = 3; 186, 199, 348); SE = 52.0 |
| 7 | 35.9 (n = 21); SE = 2.47 |
| 12 | 42.5 (n = 2; 51.0, 34.0); SE = 8.5 |
| 13 | 57.5 (n = 2; 52.0, 63.0); SE = 5.5 |

Formulation Example 1

Preparation of a Gel Containing 2% (w/w) 2-[4-methyl-2-(6-methyl-pyridin-2-yl)-2H-pyrazol-3-yl]-thieno[3,2-c]pyridine Materials:
Ethanol (200 Proof), USP (Aaper Alcohol and Chemical Co, KY)
Propylene glycol (Purity >99.5%), ACS reagent (Sigma-Aldrich Chemicals, St. Louis, Mo.)
Polyethylene glycol (PEG 400), Molecular Weight: 380-420 (Mallinkrodt Baker Inc., Phillipsburg, N.J.)
Hydroxypropyl cellulose (KLUCEL® HF) (Hercules Incorporated, Wilmington, Del.)
Water, Chromosolve® for HPLC (Sigma-Aldrich Chemicals, St. Louis, Mo.)
Benzyl alcohol (Purity >99%) (Sigma-Aldrich Chemicals, St. Louis, Mo.)

Procedure:
2-[4-Methyl-2-(6-methyl-pyridin-2-yl)-2H-pyrazol-3-yl]-thieno[3,2-c]pyridine (2 g) was transferred into a 150-mL glass bottle. Then propylene glycol (30 g), polyethylene glycol (30 g), water (10 g), and benzyl alcohol (2 g) and ethanol (20 g) were added to the bottle. The mixture was stirred for 2 hours. Then KLUCEL® HF (500 mg) was added to the solution, followed by ethanol q.s. to 100 g. The solution was stirred overnight to yield a gel containing 2% (w/w) 2-[4-methyl-2-(6-methyl-pyridin-2-yl)-2H-pyrazol-3-yl]-thieno[3,2-c]pyridine.

Formulation Example 2

Preparation of a Gel Containing 1% (w/w) 2-[4-methyl-2-(6-methyl-pyridin-2-yl)-2H-pyrazol-3-yl]-thieno[3,2-c]pyridine.

Materials:
Ethanol (200 Proof), USP (Aaper Alcohol and Chemical Co, KY) Propylene glycol (Purity >99.5%), ACS reagent (Sigma-Aldrich Chemicals, St. Louis, Mo.)
Polyethylene glycol (PEG 400), Molecular Weight: 380-420 (Mallinkrodt Baker Inc., Phillipsburg, N.J.)
Hydroxypropyl cellulose (KLUCEL® HF) (Hercules Incorporated, Wilmington, Del.)
Water, Chromosolve® for HPLC (Sigma-Aldrich Chemicals, St. Louis, Mo.)
Benzyl alcohol (Purity >99%) (Sigma-Aldrich Chemicals, St. Louis, Mo.)

Procedure:
2-[4-Methyl-2-(6-methyl-pyridin-2-yl)-2H-pyrazol-3-yl]-thieno[3,2-c]pyridine (1 g) was transferred into a 150-mL glass bottle. Then propylene glycol (30 g), polyethylene glycol (30 g), water (10 g), and benzyl alcohol (2 g) and ethanol (20 g) were added to the bottle. The mixture was stirred for 30 minutes to 1 hour. Then KLUCEL® HF (500 mg) was added to the solution, followed by ethanol q.s. to 100 g. The solution was stirred overnight to yield a gel containing 1% (w/w) 2-[4-methyl-2-(6-methyl-pyridin-2-yl)-2H-pyrazol-3-yl]-thieno[3,2-c]pyridine.

It is understood that the examples and embodiments described herein are for illustrative purposes only and that various modifications or changes in light thereof will be apparent to persons skilled in the art and are to be included within the spirit and purview of this application and the scope of the appended claims. All publications, patents, and patent applications cited herein are hereby incorporated by reference in their entirety for all purposes.

What is claimed is:

1. A method of treating a TGFβ-mediated condition, comprising administering to a mammal in need of such treatment a therapeutically effective amount of a compound of Formula I

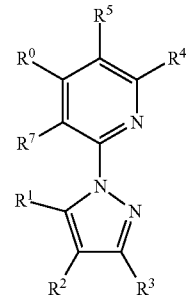

or a pharmaceutically acceptable salt thereof, wherein:

$R^1$ is a thieno[3,2-c]pyridinyl, a thieno[3,2-b]pyridinyl, thieno[2,3-c]pyridinyl, or a thieno[2,3-b]pyridinyl, each of which may be optionally substituted with one to three substituents each independently selected from the group consisting of: $C_1$-$C_3$-alkyl, —($C_1$-$C_3$-alkyl)—S—($C_1$-$C_3$-alkyl), —S—$C_1$-$C_3$-alkyl, —($C_1$-$C_3$-alkyl) -O—($C_1$-$C_3$-alkyl), —O—$C_1$-$C_3$-alkyl, —C(O)O—$C_1$-$C_3$-alkyl, —C(O)O—H, —C(O)NR$^{30}$R$^{31}$, halo, —CN, and —OH, wherein R$^{30}$ and R$^{31}$ are each independently selected from the group consisting of: H, $C_1$-$C_3$ alkyl-OH, $C_1$-$C_3$-alkyl, halo, and —O—$C_1$-$C_3$-alkyl;

$R^2$ and $R^3$ are independently selected from the group consisting of: hydrogen, $C_1$-$C_3$-alkyl, —($C_1$-$C_3$-alkyl)-S—($C_1$-$C_3$-alkyl), —S—$C_1$-$C_3$-alkyl, —($C_1$-$C_3$-alkyl)-O—($C_1$-$C_3$-alkyl), —O—$C_1$-$C_3$-alkyl, —C(O)O—$C_1$-$C_3$-alkyl, —C(O)O—H, C(O)NH$_2$, —C(O)NH($C_1$-$C_3$ alkyl), —C(O)N($C_1$-$C_3$alkyl)$_2$, halo, —CN, —OH, and a $C_3$-$C_6$-cycloalkyl, wherein R$^{30}$ and R$^{31}$ are each independently selected from the group consisting of: H, and $C_1$-$C_3$ alkyl;

or $R^2$ and $R^3$ may be taken together to form a 5 or 6 membered heteroaryl, a phenyl, a $C_4$-$C_6$-cycloalkyl, or a 4-6-membered heterocycloalkyl, wherein said $C_4$-$C_6$-cycloalkyl or 4-6-membered heterocycloalkyl may be optionally substituted with one to three substituents independently selected from halo, —OH, oxo, and $C_1$-$C_3$ alkyl, wherein said 5 or 6-membered heteroaryl, or phenyl may be optionally substituted with one to three substituents independently selected from halo, —CN, —OH, —O—$C_1$-$C_3$ alkyl and $C_1$-$C_3$ alkyl; and $R^4$, $R^5$, $R^6$, and $R^7$ are selected from the group consisting of: H, —OH, $C_3$-cycloalkyl, $C_1$-$C_3$-alkyl), —($C_1$-$C_3$-alkyl)-S—($C_1$-$C_3$ alkyl), —S—$C_1$-$C_3$-alkyl, —($C_1$-$C_3$-alkyl)-O—($C_1$-$C_3$-alkyl), —O—$C_1$-$C_3$-alkyl, —C(O)O—$C_1$-$C_3$-alkyl, —C(O)O—H, C(O)$NH_2$, —C(O)NH ($C_1$-$C_3$ alkyl), —C(O)NH(O—$C_1$-$C_3$ alkyl), —C(O)N(H)(halo), —C(O)N($C_1$-$C_3$ alkyl)$_2$, —C(O)N($C_1$-$C_3$ alkyl)(O—$C_1$-$C_3$alkyl), —C(O)N($C_1$-$C_3$ alkyl)(halo), —C(O)N(O—$C_1$-$C_3$ alkyl)$_2$, C(O)N(O—$C_1$-$C_3$ alkyl)(halo), —C(O)N(halo)$_2$, halo, —CN, and —OH; and wherein the TGFβ-mediated condition is dermal scarring.

2. The method of claim 1, wherein $R^2$ and $R^3$ are taken together to form a $C_4$-$C_6$-cyoloalkyl, or a 4-6-membered heterocycloalkyl, wherein said $C_4$-$C_6$-cycloalkyl or 4-6-membered heterocycloalkyl may be optionally substituted with one to three substituents independently selected from oxo and $C_1$-$C_3$ alkyl.

3. The method of claim 2, wherein $R^2$ and $R^3$ are taken together to form a $C_5$-cycloalkyl, or a 4-6-membered heterocycloalkyl, wherein said 4-6-membered heterocycloalkyl is selected from the group consisting of: a tetrahydrofuranyl, a tetrahydrothienyl, a imidazlidinyl, an oxazolidinyl, an imidazolinyl, an isoxazolidinyl, and a pyrrolidinyl.

4. The method of claim 3, wherein $R^1$ is a thieno[3,2-c]pyridinyl or a thieno[2,3-c]pyridinyl, which may be optionally substituted with one to three substituents each independently selected from the group consisting of: —OH, $C_1$-$C_3$ alkyl, halo, and —O—$C_1$-$C_3$alkyl.

5. The method of claim 4, wherein said compound is 2-(2-(6-methylpyridin-2-yl)-2,4,5,6-tetrahydrocyclopenta[c]pyrazol-3-yl)thieno[3,2-d]pyridine, or a pharmaceutically acceptable salt thereof.

6. The method of claim 4, wherein said compound is 2-(2-(6-methylpyridin-2-yl)-2,4,5,6-tetrahydrocyclopenta[c]pyrazol-3-yl)thieno[2,3-c]pyridine, or a pharmaceutically acceptable salt thereof.

7. The method of claim 1, wherein $R^2$ and $R^3$ are independently selected from the group consisting of: hydrogen, $C_1$-$C_3$-alkyl, —($C_1$-$C_3$-alkyl)-O—($C_1$-$C_3$-alkyl), —O—$C_1$-$C_3$-alkyl, —C(O)O—$C_1$-$C_3$ alkyl, —C(O)O—H, C(O)$NH_2$, —C(O)NH($C_1$-$C_3$ alkyl), —C(O)N($C_1$-$C_3$alkyl)$_2$, halo, —CN, —OH, and a $C_3$-$C_1$-cycloalkyl.

8. The method of claim 7, wherein $R^2$ and $R^3$ are independently selected from the group consisting of: hydrogen, and $C_1$-$C_3$ alkyl.

9. The method of claim 8, wherein $R^2$ is $C_1$-$C_2$ alkyl and $R^3$ is hydrogen.

10. The method of claim 9, wherein $R^5$, $R^6$, and $R^7$ are H, and $R^9$ is $C_1$-$C_3$-alkyl.

11. The method of claim 10, wherein $R^4$ is methyl.

12. The method of claim 11, wherein $R^1$ is a thieno[3,2-c]pyridinyl or a thieno[2,3-c]pyridinyl, which may be optionally substituted with one to three substituents each independently selected from the group consisting of: —OH, $C_1$-$C_3$ alkyl, halo, and —O—$C_1$-$C_3$ alkyl.

13. The method of claim 12, wherein $R^1$ is a thieno[3,2-c]pyridin-2-yl or a thieno[2,3-c]pyridin-2-yl, which may be optionally substituted with one to three substituents each independently selected from the group consisting of: —OH, $C_1$-$C_3$ alkyl, halo, and —O—$C_1$-$C_3$ alkyl.

14. The method of claim 13, wherein $R^1$ is a thieno[3,2-c]pyridin-2-yl.

15. The method of claim 1, wherein said compound is selected. from the group consisting of:
2-[1-(6-methylpyridin-2-yl)-1H-pyrazol-5-yl]thieno[3,2-c]pyridine;
2-[3,4-dimethyl-1-(6-methylpyridin-2-yl)-1H-pyrazol-5-yl]thieno[3,2-c]pyridine;
2-[3-methyl-1-(6-methylpyridin-2-yl)-1H-pyrazol-5-yl]thieno[3,2-c]pyridine;
2-[3-ethyl-1-(6-methylpyridin-2-yl)-1H-pyrazol-5-yl]thieno[3,2-c]pyridine;
2-[4-ethyl-1-(6-methylpyridin-2-yl)-1H-pyrazol-5-yl]thieno[3,2-c]pyridine; and
pharmaceutically acceptable salts thereof.

16. The method of claim 1, wherein said compound is 2-[4-methyl-1-(6-methylpyridin-2-yl)-1H-pyrazol-5-yl]thieno[3,2-c]pyridine; or a pharmaceutically acceptable salt thereof.

17. The method of claim 13, wherein $R^1$ is a thieno[2,3-c]pyridin-2-yl.

* * * * *